United States Patent [19]

Barton et al.

[11] 4,078,139

[45] Mar. 7, 1978

[54] PROCESS FOR DEOXYGENATING SECONDARY ALCOHOLS

[75] Inventors: Derek H. R. Barton, London, England; Stuart W. McCombie, West Orange, N.J.

[73] Assignee: Schering Corporation, Kenilworth, N.J.

[21] Appl. No.: 704,703

[22] Filed: Jul. 12, 1976

Related U.S. Application Data

[63] Continuation-in-part of Ser. No. 600,704, Jul. 31, 1975, abandoned.

[51] Int. Cl.$^2$ .................. C07H 15/22; C07J 31/00
[52] U.S. Cl. ............................... 536/17; 260/397.2; 260/397.4; 260/397.5; 260/429 R; 260/429.7; 260/452; 260/455 R; 260/463; 260/596; 260/603 R; 260/638 R; 260/666 R; 424/180; 424/181; 424/182; 536/1; 536/4; 536/10; 536/26; 536/115; 536/121; 560/106; 548/341
[58] Field of Search ................. 536/17, 1, 17 R, 4; 260/491 R, 638 R

[56] References Cited

U.S. PATENT DOCUMENTS

| 3,828,021 | 8/1974 | Beattie et al. | 536/17 |
| 3,868,360 | 2/1975 | Daniels et al. | 536/17 |
| 3,920,628 | 11/1975 | Daniels | 536/17 |

OTHER PUBLICATIONS

Perkins, "J. Chem. Soc.," No. 16, pp. 1574–1585, 1975.
Hitoshi, et al., "Chem. Abst.," vol. 76, 1972, pp. 127, 293x.

Primary Examiner—Johnnie R. Brown
Attorney, Agent, or Firm—Mary S. King; Stephen B. Coan

[57] ABSTRACT

The process for removing a secondary hydroxyl group from an organic compound having at least one secondary hydroxyl group and having any amino groups protected, comprises the reaction of a reactive ester of said secondary hydroxyl group selected from the group consisting of an O-alkylthioester and an O-alkylselenoester with at least one mole of an organotin hydride, preferably tri-n-butylstannane, in an inert, aprotic solvent at a temperature of at least about 100° C and under an inert atmosphere.

The process is particularly useful in removing secondary alcohols in aminoglycoside antibiotics to produce deoxy derivatives thereof having antibacterial activity.

Also described are novel O-sec.-alkylthiobenzoate, O-sec.-alkyl-S-methylxanthate, N-(sec.-alkoxythiocarbonyl)-imidazole esters, and di-O-alkylthiocarbonates having at least one secondary O-alkyl group, useful intermediates of the claimed process.

10 Claims, No Drawings

PROCESS FOR DEOXYGENATING SECONDARY ALCOHOLS

CROSS-REFERENCE TO RELATED APPLICATIONS

This application is a continuation-in-part of copending application Ser. No. 600,704 filed July 31, 1975, now abandoned.

FIELD OF INVENTION

This invention relates to a novel process and to intermediates useful therein.

More specifically, this invention relates to a process for removing secondary hydroxyl groups from an organic compound and to novel O-alkylthioester and O-alkylselenoester intermediates useful therein.

In particular, this invention relates to a process for removing a secondary hydroxyl group from an aminoglycoside antibacterial agent by reaction of an O-alkylthioester or an O-alkylselenoester of said secondary alcohol with an organotin hydride whereby is obtained a deoxy derivative of said aminoglycoside having antibacterial activity.

DESCRIPTION OF THE PRIOR ART

In general, prior art methods of removing primary or secondary alcohol groups involve conversion of the alcohol into a sulfonate ester, e.g., a p-toluenesulfonate or a methanesulfonate ester, followed either by direct reduction thereof or via an appropriate halide or sulfur displacement derivative followed by reduction thereof. These methods are ionic in nature and work well on primary alcohols and reasonably well on unhindered secondary alcohols. However, when removing a hindered secondary alcohol, such as found in sugars and in aminoglycosides, by these prior art processes, competing reactions take place with concomitant poor yields of desired deoxy product.

The process of this invention provides a deoxygenation process carried out under neutral conditions, the mechanism of which is radical in nature and, thus, avoids the competing rearrangement reactions encountered in prior art carbonium ion and displacement reactions. Specifically, by our process, reaction of an O-alkylthioester or an O-alkylselenoester of a secondary alcohol, including hindered secondary alcohols, with an organotin hydride, particularly tri-n-butylstannane, produces good yields of the corresponding deoxy derivative.

Our process is particularly useful in producing selectively deoxygenated derivatives of polyhydroxylated antibiotics having useful antibacterial activity.

By our invention we have also developed a convenient general synthesis of O-alkylthioesters and O-alkylselenoesters, whereby are prepared novel esters of aminoglycosides, which are valuable intermediates in the deoxygenation process of this invention.

GENERAL DESCRIPTION OF THE DEOXYGENATION PROCESS OF THE INVENTION

The invention sought to be patented in its process aspect resides in the concept of a process for removing a secondary hydroxyl group from an organic compound having at least one secondary hydroxyl group and having any amino groups protected, which comprises the reaction of a reactive ester of said secondary hydroxyl group selected from the group consisting of an O-alkylthioester and an O-alkylselenoester with at least one mole of an organotin hydride in an inert, aprotic solvent at a temperature of at least 100° C and under an inert atmosphere, whereby is formed the corresponding deoxy derivative.

The organotin hydride reagents and their method of preparation are well known in the art. For use in our process, the organotin hydride reagent may contain any organic radical of any molecular weight, including alkyltin hydrides (e.g. trimethyltin hydride and triethyltin hydride), aryltin hydrides (e.g. triphenyltin hydride) and aralkyltin hydrides (e.g. tri-benzyltin hydride). A preferred reagent for use in our process is tri-n-butyltin hydride.

Requisite intermediates of our process are O-alkylthioesters and O-alkylselenoesters of the secondary hydroxyl group to be removed from a given organic compound. Of these, O-alkylthioesters are the preferred intermediates since they lead to greater yields of purer deoxygenated product than do the corresponding O-alkylselenoesters.

The requisite O-alkylthioester intermediates of our process are compounds defined by the following structural formula I:

$$R-O-\overset{\overset{S}{\|}}{C}-X \qquad (I)$$

wherein R is the radical of an organic compound bonded to the oxygen by a methine carbon; and X may be hydrogen or any aliphatic, alicyclic or aromatic radical which may contain hetero atoms which are not reduced by an organotin hydride. Thus, the substituent X, in formula I, is advantageously devoid of nitro, nitroso, chlorine, bromine and iodine.

The substituent X in formula I may be bonded to the thiocarbonyl group through a carbon atom or through a hetero atom such as nitrogen or sulfur. Thus, included among the O-alkylthioester intermediates of this invention are those wherein X is hydrogen, alkyl, aryl, aralkyl, and hetero substituted derivatives thereof. Of these, O-alkylthioesters of formula I which are particularly useful in our process are those wherein X is phenyl, 1-imidazolyl

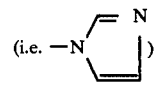

and —S—CH$_3$ which are identified as O-sec.-alkylthiobenzoates, N-(sec.-alkoxythiocarbonyl)imidazoles, and as O-sec.-alkyl-S-methylxanthates, respectively. Of these, we have found that O-sec.-alkylthiobenzoate esters are preferred when removing secondary hydroxyl groups from aminoglycosides, since they lead to greater yields of desired deoxygenated product.

The O-alkylselenoester intermediates of our process of compounds of following formula II:

$$R-O-\overset{\overset{Se}{\|}}{C}-X' \qquad (II)$$

wherein R is as defined for formula I, and X' is an aromatic radical, preferably phenyl.

Other O-alkylthioester intermediates of this process are compounds of following formula III:

wherein R is the radical of an organic compound bonded to the oxygen by a methine carbon and X″ is either an aliphatic, alicyclic or aromatic radical which may contain hetero atoms, or is a chemical bond to a carbon atom of the radical R, which carbon atom is in position $\alpha$ or $\beta$ relative to the said methine carbon. Thus, the compounds of formula III embrace acyclic and cyclic thioesters. In both cases, the reaction with the organotin hydride is effected in the presence of a radical initiator. Any radical initiator may be used which decomposes at about 100° C, such as dibenzoyl peroxide or azobisisobutyronitrile.

The cyclic thioesters of formula III are diol thiocarbonate esters and can be used only when the starting compounds have either vicinal or neighboring (i.e. are spatially adjacent) hydroxyl groups. However, only one hydroxyl group of the two hydroxyl groups forming the thiocarbonate is removed by our process. After reduction with the organotin hydride, alkaline hydrolysis is required as a final step to remove the residual thiocarbonate ester formed at the hydroxy group which is not removed during the reaction.

If both hydroxyl groups (vicinal or neighboring) which give rise to formation of the thiocarbonate ester, are secondary hydroxyls, deoxygenation will, in general, not be selective at one position, and the reaction mixture will contain mono-deoxygenated compounds wherein either one or the other of the above two hydroxyl groups is removed. If one of the hydroxyl groups is a primary hydroxyl group and the other secondary, deoxygenation occurs preferentially at the secondary hydroxyl group.

The temperature at which our process is preferably carried out is at least about 100° C in order that the intermediate formed upon reaction of an organotin hydride with an O-alkylthioester or O-alkylselenoester will fragment to form the desired deoxy compound. The process may be carried out at temperatures lower than 100° C, albeit in smaller yields. The upper limit of the temperature range at which our process is advantageously carried out is determined by the temperature at which the O-alkylthio (or seleno) ester will decompose.

Solvents useful in our process are preferably aprotic solvents which boil above 100° C, preferably in the range of 100° to 150° C. Toluene or xylene are usually employed. The solvent need not be anhydrous, but too much (i.e. over 0.5%) water ought not be present.

Our process is carried out in an inert atmosphere such as argon or nitrogen.

The starting compounds of our process may be any organic compound containing at least one secondary alcohol in which any amino groups present are protected, preferably by benzyloxycarbonyl, substituted benzyloxycarbonyl (including o, m, and p-methoxybenzyloxycarbonyl, 4-decyloxybenzyloxycarbonyl, mesityloxycarbonyl), alkoxycarbonyl (e.g. methoxycarbonyl, n-butoxycarbonyl, tert.-butoxycarbonyl, octyloxycarbonyl), and lower alkanoyls (e.g. acetyl, propionyl, valeryl, caprylyl). Methods whereby the foregoing amino protected derivatives are prepared from the free amine as well as methods of converting an N-protected derivative to a free amino compound are well known in the art.

The secondary hydroxylated starting compounds are also preferably devoid of substituents which are reduced by organotin hydrides such as nitro, nitroso, chlorine, bromine and iodine unless one wishes to concomitantly remove a secondary hydroxyl group and reduce any other reducible function in the compound.

Tertiary hydroxyl groups and secondary hydroxyl groups other than the secondary hydroxyl group to be removed by our process need not be protected prior to reaction with an organotin hydride; however, when other secondary hydroxyl functions are protected prior to preparation of the requisite thioester or selenoester intermediate, the yields of desired deoxygenated compounds are greater than when the other secondary hydroxyl functions are unprotected. Any primary hydroxyl functions present in the organic starting compounds in our process ought be protected (provided it is not required for formation of the cyclic thioesters of formula III) since primary alcohols form O-alkylthioesters and O-alkylselenoesters which, under the conditions of our process, will also deoxygenate, albeit in small yields. Useful O-protecting groups for any primary and other secondary hydroxyl groups in the organic starting compound of the process of this invention include hydrocarboncarbonyl (e.g. benzoyl, acetyl, propionyl); alkoxycarbonyl (e.g. methoxycarbonyl, ethoxycarbonyl); aralkoxycarbonyl (e.g. benzyloxycarbonyl); cyclic ketals and cyclic acetals of neighboring hydroxyl groups including O-alkylidenes (e.g. O-isopropylidene), O-cycloalkylidenes (e.g. O-cyclohexylidene) and O-aralkylidene (e.g. O-benzylidene) derivatives; carbonyl derivatives of neighboring hydroxyl and amino functions (which, in essence, are cyclic carbonates and carbamates, respectively) and hydrolyzable ethers of primary hydroxyl groups (e.g. triphenylmethyl ether). Processes for preparing the foregoing O-protected derivatives as well as processes whereby they are removed to regenerate the free hydroxyl groups are well known in the art.

The starting compound of our process, thus, may be any organic compound having a secondary alcohol wherein the oxygen is bonded to a methine carbon, and includes sec.-alkanols, (e.g. isopropanol); sec.-cycloalkanols (e.g. ciscyclohexanediol); steroidal alcohols (e.g. 5$\alpha$-cholestanol, cholesterol, 9$\alpha$-fluoro-11$\beta$-hydroxyprogesterone, dexamethasone); secondary hydroxylated sugars (e.g. $\alpha$-D-glucofuranose, $\beta$-Dgalactose, D-altrose, and $\alpha$D-glucopyranose) all of which are convertible by our process to the corresponding deoxygenated derivative.

Our process is particularly useful in selectively deoxygenating secondary hydroxyl functions in aminoglycoside antibacterial agents to produce deoxy derivatives thereof which also possess antibacterial activity. Thus, by our process, reaction of the 3′-thiobenzoate ester of 1,3,2′-tri-N-ethoxycarbonyl-5,6,4′-di-O-isopropylideneparomamine with tri-n-butylstannane in toluene at reflux temperature followed by removal of the amino and hydroxyl protecting groups produces the known antibacterial agent, 3′-deoxyparomamine, in good yields.

Similarly, reaction of the 3′-thiobenzoate ester of 1,3,2′-tri-N-benzyloxycarbonyl-5,6-O-cyclohexylidene-4,′,6′-O,N-carbonylneamine with tri-n-butylstannane in refluxing toluene according to our process, followed by removal of the amino and hydroxy protecting groups produces the known antibacterial agent, 3-deoxyneamine, in good yields.

A preferred mode of our process is that wherein a secondary hydroxyl function in a pseudotrisaccharide is selectively removed to produce other known pseudotrisaccharide antibacterial agents. Thus, for example, the 2″-O-thiobenzoate ester of each of 1,3,2′,6′,3″-penta-N-benzyloxycarbonylgentamicin C$_2$ and 1,3,2′,6′,3″-penta-N-benzyloxycarbonylsisomicin, upon reaction with tri-n-butyltin hydride in refluxing toluene followed by removal of the amino protecting benzyloxycarbonyl groups, as described in Examples 13 and 14, yields 2″-deoxygentamicin C$_2$ and 2″-deoxysisomicin, respectively, which are antibacterial agents described and claimed in U.S. Pat. No. 3,920,628. By our process, there may also be prepared the 2″-deoxy derivatives of gentamicins A, C$_1$, C$_{1a}$, C$_{2a}$, X$_2$, of verdamicin, Antibiotic JI-20A, Antibiotic JI-20B and Antibiotic G-418.

Similarly, by reacting the 3′-O-thiobenzoate ester of 1,3,6′,3″-tetra-N-benzyloxycarbonylgentamicin B with tri-n-butylstannane refluxing toluene followed by removal of the amino protecting groups, there is produced 3′-deoxygentamicin B, an antibacterial agent described in South African Pat. No. 73,7780 and British Pat. No. 1,420,879.

Similarly, by reacting the 4′-O-thiobenzoate ester of 1,3,6′,3″-tetra-N-ethoxycarbonyl-2′,3′;4″,6″-di-O-isopropylidene-2″-O-tetrahydropyranylkanamycin A with tri-n-butylstannane in refluxing toluene followed by removal of the protecting groups, there is produced 4′-deoxykanamycin A, an antibacterial agent described in U.S. Pat. No. 3,886,138.

Antibiotics JI-20A and JI-20B have vicinal secondary hydroxyl groups at the 3′ and 4′ positions and other secondary hydroxyl groups at C-5 and C-2″. As described in Preparation 11 and in Examples 15 and 16, after protecting the amino functions by a benzyloxycarbonyl or an ethoxycarbonyl group and the 3′,4′-hydroxyl groups by a ketal, the 2″-hydroxyl group is protected by preparing an O-benzoate ester thereof. The ketal function at C-3′ and 4′ is then removed and the O-thiobenzoate ester of the free 3′ and 4′ secondary hydroxyl groups are prepared and separated (the hindered 5′-hydroxyl function remaining unesterified) followed by reaction of each of the resulting 3′-O-thiobenzoyl or 4′-O-thiobenzoyl derivative with tri-n-butylstannane in refluxing toluene according to our process to produce good yields of each of 3′-deoxy- Antibiotic JI-20A; 3′-deoxy-Antibiotic JI-20B; 4′-deoxy-Antibiotic JI-20A and of 4′-deoxy-Antibiotic JI-20B. When preparing the 3′- and 4′-deoxy derivatives of Antibiotic JI-20B, we found the best yields of deoxy product were obtained when the 3′- or 4′-O-thiobenzoate derivative was added to an excess of tri-n-butylstannane. The foregoing 3′- and 4′-deoxy derivatives are all antibacterial agents, of which 3′-deoxy-Antibiotic JI-20A is specifically described in British Pat. No. 1,420,879. To convert Antibiotic JI-20B to 3′,4′-dideoxy-Antibiotic JI-20B (an antibiotic known in the art as gentamicin C$_{2a}$), by our process, one only has to prepare the O-thiobenzoate ester of the remaining secondary hydroxyl group in either 3′-deoxy or 4′-deoxy-Antibiotic JI-20B having amino protecting groups and react said ester with tri-n-butylstannane. Similarly, Antibiotic JI-20A may be converted to gentamicin C$_{1_a}$ (3′,4′dideoxy-Antibiotic JI-20A) by first removing one of the vicinal secondary hydroxyl functions as described herein and then preparing the O-thiobenzoate ester of the remaining hydroxyl group followed by treatment thereof with tri-n-butylstannane.

One also can prepare the 3′,4′-di-O-thiocarbonyl derivative of per-N-protected-2″-O-protected Antibiotic JI-20B which, upon reaction with tri-n-butylstannane in refluxing toluene in the presence of azobisisobutyronitrile followed by alkaline hydrolysis yields a mixture of 3′-deoxy-Antibiotic JI-20B and 4′-deoxy-Antibiotic JI-20B which can be separated according to methods known in the art. Similarly, 3′-deoxy-Antibiotic JI-20A and 4′-deoxy-Antibiotic JI-20A can be prepared from the corresponding 3′,4′-di-O-thiocarbonyl intermediate.

In general, when carrying out our process, a solution of an O-alkylthioester or of an O-alkylselenoester (preferably an O-alkylthioester, particularly an O-thiobenzoate) of a secondary alcohol in toluene is added dropwise to a stirred solution of an organotin hydride (preferably tri-n-butylstannane) in toluene at reflux temperature, the quantity of said organotin hydride being at least equimolar to the quantity of secondary alcohol (usually 1.5 to 3 moles of tri-n-butylstannane is used per mole of the secondary alcohol ester). The reaction is continued until the intermediary ester is no longer present as determined by thin layer chromatography (usually 1 to 8 hours) then the deoxy compound is isolated utilizing conventional techniques after removing any protecting groups which are present.

ESTER INTERMEDIATES AND METHODS FOR THEIR PREPARATION

In general, the O-alkylthioester intermediates of this invention are prepared from the corresponding secondary alcohol (having any amino groups protected and any primary hydroxyl groups protected and optionally having other secondary hydroxyl groups protected) utilizing methods known in the art. Thus, the N-(sec.-alkoxycarbonyl)imidazole ester intermediates of this invention, i.e. those of formula II wherein X is

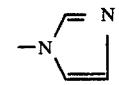

are prepared according to known procedures by reacting an organic compound having a secondary alcohol (e.g. cholestanol) with N,N′-thiocarbonyldiimidazole in an inert solvent (e.g. 1,2-dichloroethane or toluene) whereby is produced the imidazole ester (e.g. N-(3β-cholestanyloxythiocarbonyl)imidazole).

Similarly, the O-sec.-alkyl-S-methylxanthate ester intermediates, i.e. those of formula I wherein X is —SCH$_3$, are prepared by the reaction of the corresponding secondary alcohol (e.g. cholesterol) in tetrahydrofuran with excess sodium hydride containing a trace of imidazole as catalyst for alkoxide formation, followed by reaction with excess carbon disulfide and then alkylation of the xanthate salt thereby formed with excess iodomethane or dimethylsulfate whereby is produced the corresponding S-methyl-xanthate ester (e.g. O-cholesteryl-S-methylxanthate).

The O-alkylthioesters for formula I wherein X is H, alkyl, aryl or aralkyl are conveniently prepared via an "amido chloride" route shown below in Diagram A wherein R is as defined for formula I:

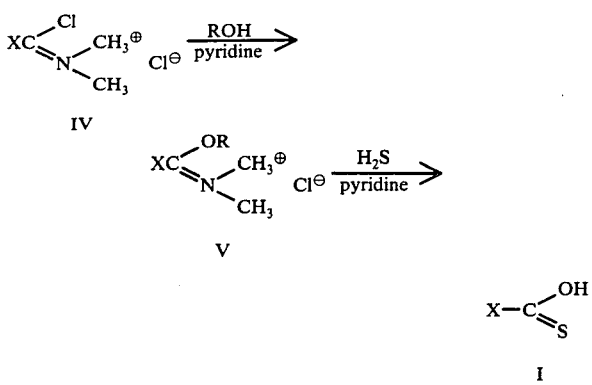

Diagram A

By this process, a "Vilsmeier salt" (IV) is prepared by reaction of phosgene with an appropriate N,N'-dialkyl acid amide, and condensed with a secondary alcohol followed by treatment of the resulting imidinium chloride salt (V) with base and hydrogen sulfide. In this procedure, an excess of Vilsmeier salt is usually employed. Thus, when preparing an O-thiobenzoate ester intermediate (i.e. a compound of formula I wherein X is phenyl), upon reaction of N,N-dimethylbenzamide and phosgene in dichloromethane at room temperature there is produced N,N-dimethyl-β-chlorobenzimidinium chloride (compound of formula IV wherein X is phenyl) which, upon reaction with an organic compound containing a secondary hydroxyl function (e.g. 1,3,2′,6′,3″-penta-N-benzyloxycarbonylgentamicin C$_2$) followed by reaction of the imidinium chloride salt thereby produced (e.g. 1,3,2′,6′,3″-penta-N-benzyloxycarbonyl-2″-O-(N,N- dimethyl benzimidinium chloride)gentamicin C$_2$) (a compound of formula V wherein X is phenyl and R is the N-protected gentamicin C$_2$ radical) with hydrogen sulfide in pyridine whereby is produced an O-sec.-alkylthioester of formula I wherein X is phenyl (e.g. 1,3,2′,6′,3″-penta-N-benzyloxycarbonyl-2″-O-thiobenzoylgentamicin C$_2$).

In gentamicin C$_2$ there is a tertiary hydroxyl group at C-4″ and hydroxyl function at C-5 as well as at the 2″-position; however, reaction of the O-unprotected-per-N-protected-gentamicin C$_2$ produced excellent yields (82% theory) of the desired 2″-O-thiobenzoyl ester. The 2″-hydroxyl function is the least hindered secondary hydroxyl group and thus more available for esterification. Once esterified at the 2″-position, the positively charged imidium chloride intermediate, in effect, repels further attack on the same molecule by the positively charged N,N-dimethyl-β-chlorobenzimidinium chloride (III) and thus diminishes the chances of further reaction with another secondary alcohol in the same molecule.

When more than one secondary alcohol is present in an organic compound and one wishes to remove the more hindered secondary alcohol, then one must protect the less hindered secondary alcohol prior to exterification by the procedure outlined herein above.

Thus, when removing the 3′- or 4′-secondary hydroxyl function in Antibiotics JI-20A or JI-20B, which also has a secondary alcohol at C-2″ and a more hindered secondary alcohol at C-5, after protecting all the amino functions therein, it is necessary to protect the 2″-hydroxyl group such as by esterification thereof prior to reaction with a Vilsmeier salt and thence treatment with hydrogen sulfide.

In similar manner to that described in detail hereinabove, O-sec.-alkylthioformates and O-sec.-alkylthioalkanoates (esters of formula I wherein X is hydrogen and lower alkyl, respectively) can be formed. Thus, for example, reaction of N,N'-dimethylformamide or N,N'-dimethylacetamide with phosgene produces N,N'-dimethyl-β-chloroformimidinium chloride and N,N'-dimethyl-β-chloroacetimidinium chloride, respectively (compounds of formula III wherein X is hydrogen and methyl, respectively) which, upon reaction with secondary alcohol produces the corresponding imidinium chloride intermediate (IV) which, upon reaction with hydrogen sulfide yields an O-sec.-alkylthioformate and an O-sec.-alkylthioacetate ester, respectively (formula I, X=H or methyl).

In general, the O-alkylthioester intermediates of formula III are prepared from the corresponding secondary alcohol utilizing methods known in the art. The cyclic diol thiocarbonate esters may be prepared as described by D. H. R. Barton and R. V. Stick in *J. Chem. Soc., Perk. I*, 1773–1776 (1975). Thus, diol thiocarbonate ester intermediates, i.e. those of formula III, wherein X″ is a chemical bond, are prepared by reacting an organic compound having vicinal (α,β) or neighboring (α,γ) hydroxyl groups (e.g. 1,2-O-isopropylidene-3-O-methyl-α-D-glucofuranose) with N,N″-thiocarbonyldiimidazole in an inert solvent, whereby is produced the thiocarbonate ester (e.g. 1,2-O-isopropylidene-3-O-methyl-5,6-O-thiocarbonyl-α-D-glucofuranose). The acyclic ester intermediates of formula III may be prepared from intermediates of formula I, wherein X is a radical which is bonded to the thiocarbonyl group through a nitrogen or sulfur atom, preferably from N-(sec.-alkoxycarbonyl)imidazole ester intermediates (e.g. from N-(3β-cholestanyloxythiocarbonyl)-imidazole) by quaternizing the imidazole moiety (e.g. by alkylating with a strong alkylating agent, such as triethyloxonium fluoroborate) followed by replacement thereof with the desired —O—X″ group using the alkali metal salt of HOX″ (e.g. with sodium methylate in methanol to give O-methyl-O-3β-cholestanyl thiocarbonate).

O-Alkylselenoesters of formula II are novel compounds and are prepared by the reaction of the secondary alcohol imidinium chloride intermediate (V') (prepared as described hereinabove as shown in Diagram A) with sodium hydroselenide, which is prepared by reaction of elemental selenium with sodium borohydride, i.e. as indicated below in Diagram B:

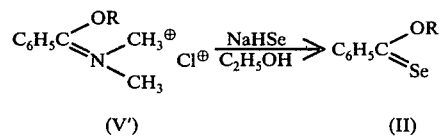

(V')        (II)

Usually, when preparing an O-sec.-alkylselenobenzoate ester of our invention, sodium hydroselenide is made according to known procedures by reaction of selenium powder and sodium borohydride in ethanol. To the resulting reaction mixture at 0° C containing triethoxyborane in addition to sodium hydroselenide, there is added acetic acid and then the benzimidinium chloride salt (V') intermediate (e.g. O-cholesteryl-N-N-dimethylbenzimidinium chloride) and the reaction solution stirred at room temperature for about 30 minutes. The O-sec.-alkylselenobenzoate ester (e.g. O-cholesterylselenobenzoate thereby formed is then conveniently isolated and purified by utilizing conventional techniques such as extraction, recrystallization and chromatographic techniques.

As discussed hereinabove, the process of this invention proceeds via a mechanism whereby the carbon-oxygen bond is cleaved in a radical fashion to give a carbon radical which is quenched by hydrogen atom transfer from the organotin hydride donor. By our process, the deoxygenation is advantageously carried out under neutral, relatively mild conditions which do not affect any other carbonyl, ester, lactone or polyene functions, which may be present in the molecule. We believe the mechanism of the process of our invention may be depicted as shown below in Diagram C for thioesters of formulae I and III:

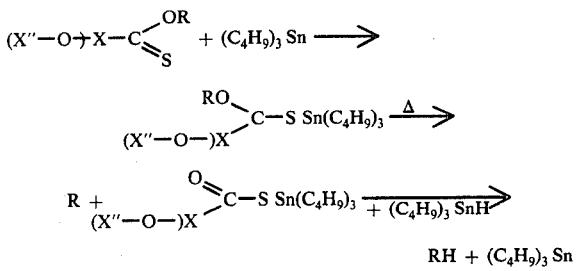

Diagram C

The method of carrying out our inventive process is illustrated in the Preparations and Examples which follow. The scope of our invention, however, is not to be construed as limited by the specific embodiments described herein since obvious modifications of our process will be suggested by these examples and the teaching in the specification to one skilled

PREPARATION OF INTERMEDIATES

PREPARATIONS 1

IMIDAZOLIDE DERIVATIVES OF CHOLESTANOL, CHOLESTEROL AND OF LANOSTEROL

A. N-(3β-Cholestanyloxythiocarbonyl)Imidazole

Dissolve cholestanol (2.5 gm.) and N,N'-thiocarbonyldiimidazole (2 gm.) in 1,2-dichloroethane (25 ml.) and heat at reflux temperature for 3 hours. Evaporate the solution in vacuo, add water to the resultant residue and extract with dichloromethane, wash the combined organic extracts with dilute hydrochloric acid, then with aqueous sodium bicarbonate and finally with water. Dry the solution over anhydrous magnesium sulfate and evaporate in vacuo to a residue comprising N-(3β-cholestanyloxythiocarbonyl)imidazole. Purify by crystallizing and recrystallizing from ether/methanol; yield 2.92 gm. (90% theory); m.p. 151°–152° C; $[\alpha]_D^{20} -57.2°$, (c=0.8, chloroform); $\lambda_{max}$ 278 nm ($\epsilon$=9,600); Combustion analysis: found: C, 74.6; H, 9.9; N, 5,65; S, 6.4. $C_{31}H_{50}N_2OS$, requires C, 74.65; H, 10.1; N, 5.6; S, 6.4%.

B. N-(3β-Cholesteryloxythiocarbonyl)Imidazole

Dissolve cholesterol (1 gm.) and N,N'-thiocarbonyldiimidazole (1 gm.) in 7 ml. of tetrahydrofuran and heat at reflux temperature for 4 hours. Evaporate the reaction mixture in vacuo, add water to the resultant residue, extract the aqueous mixture with dichloromethane, wash the combined organic extracts with dilute hydrochloric acid, then with sodium bicarbonate, then with water. Dry the solution over anhydrous magnesium sulfate and evaporate in vacuo to a residue comprising N-(3β-cholesteryloxythiocarbonyl)imidazole. Purify by recrystallizing from ether/ethanol; yield 1.15 gm. (87% theory); m.p. 144°–145° C; $[\alpha]_D^{20} -32.6°$ (c=3, chloroform); $\lambda_{max}$ 278 nm ($\epsilon$=9,600); Combustion analysis: found: C, 75.2; H, 9.5; N, 5.5; S, 6.3. $C_{31}H_{41}N_2OS$ requires C, 75.0; H, 9.7; N, 5.6; S, 6.4%.

C. N-(3β-Lanosteryloxythiocarbonyl)Imidazole

In a manner similar to that described in Preparations 1A and 1B treat lanosterol (0.5 gm.) in 1,2-dichloroethane (5 ml.) with N,N'-thiocarbonylimidazole (0.35 gm.). Isolate and purify the resultant product in a manner similar to that described to obtain N-(3β-lanosteryloxythiocarbonyl)imidazole; yield 0.49 gm. (82% theory). Purify by recrystallizing from acetone/ethanol; m.p. 162°–164° C; $[\alpha]_D^{20} + 11.1°$ (c=3, chloroform); $\lambda_{max}$ 279 nm ($\epsilon$=9,400); Combustion analysis: found: C, 75.9; H, 9.8; N, 5.1; S, 5.8. $C_{34}H_{52}N_2OS$ requires C, 76.1; H, 9.8; N, 5.7; S, 6.0%.

PREPARATION 2

THIOBENZOATE DERIVATIVES OF CHOLESTANOL, CHOLESTEROL AND LANOSTEROL

A. O-Cholesteryl Thiobenzoate (1) To dichloromethane (40 ml.) containing phosgene (5 gm.) add N,N-dimethylbenzamide (4.5 gm.) and allow the solution to stand at room temperature for 17 hours, then evaporate in vacuo. Dissolve the resultant residue in dichloromethane (40 ml.) and add this solution to a stirred solution of cholesterol (7.72 gm.) in tetrahydrofuran (50 ml.). Continue stirring for 10 minutes the reaction mixture from which the intermediate condensation product (i.e. O-cholesteryl-N,N-dimethylbenzimidinium chloride) crystallizes. Add 7 ml. of pyridine, then bubble hydrogen sulfide through the reaction mixture for 5 minutes. Dilute the reaction mixture with water, separate the layers, extract the aqueous layer with dichloromethane, wash the combined organic layer and washes with hydrochloric acid, then with aqueous sodium bicarbonate and finally with water. Dry over anhydrous magnesium sulfate, evaporate in vacuo and recrystallize the resultant residue from dichloromethane/ethanol to give O-cholesteryl thiobenzoate; yield 9.1 gm. (90% theory).

(2) In the above procedure, the intermediate condensation product may be isolated as follows. Allow a solution of N,N-dimethylbenzamide in 3.1 gm. in dichloromethane (40 ml.) containing phosgene (4 gm.) to stand overnight at room temperature, then evaporate in vacuo. Dissolve the resultant residue in dichloromethane (30 ml.)., add cholesterol (7.7 gm.) in tetrahydrofuran (40 ml.), then add anhydrous ether (60 ml.). Allow the solution to stand thirty minutes. Separate the resultant precipitate by filtration, wash with ether and dry in vacuo at 40° C to obtain O-cholesteryl-N,N-dimethylbenzimidinium chloride; yield 10.2 gm. (94% theory); m.p. 120°–125° C (dec.); $[\alpha]_D^{20} - 21°$ (c=2, chloroform).

B. O-Lanosteryl Thiobenzoate (1) In a manner similar to that described in Preparation 2A(1) treat N,N-dimethylbenzamide 81.5 gm.) with phosgene in dichloromethane for 17 hours, then evaporate the reaction mixture, dissolve the resultant residue in 5 ml. of dichloromethane, add lanosterol (3.52 gm.) in tetrahydrofuran (5 ml.) and stir the reaction mixture for 5 hours. Add 40 ml. of dichloromethane to the reaction mixture, add 3 ml. of pyridine and bubble dry hydrogen sulfide through the reaction mixture for 10 minutes, then leave the reaction mixture at room temperature for 1 hour. Isolate the resultant product in a manner similar to that described in Example 2A(1) to obtain a residue comprising O-lanosteryl thiobenzoate. Purify by boiling in methanol (50 ml.), cooling the mixture and separating the resultant precipitate by filtration; yield 2.87 gm. (92% theory); m.p. 188°–190° C; $[\alpha]_D^{20}$ − 49.9 (c=2, chloroform); $\lambda_{max}$ 418, 294 and 255 nm ($\epsilon$=150; 11,700 and 11,500); Combustion analysis: found: C, 80.5; H, 10.1; S, 5.9. $C_{36}H_{54}OS$ requires C, 80.4; H, 10.4; S, 6.1%.

(2) Alternatively, the compound of this preparation may be prepared as follows. To thiobenzoylthioglycollic acid (2.12 gm.) in tetahydrofuran (50 ml.) add with stirring sodium hydride (60% dispersion; 1 gm.) and imidazole (1.3 gm.). Heat the reaction solution at reflux temperature for 1 minutes, add a solution of lanosterol (4 gm.) in tetrahydrofuran (50 ml.) and continue heating at reflux temperature for 2 hours. Add additional thiobenzoylthioglycollic acid (1.0 gm.) and sodium hydride (0.25 gm.) in tetrahydrofuran (20 ml.) and continue heating the reaction mixture at reflux temperature for an additional 2 hours. Cool, slowly add glacial acetic acid (5 ml.), then evaporate in vacuo. Add water to the resultant residue, extract the residue with dichloromethane, wash the combined organic extracts with dilute hydrochloric acid, aqueous sodium bicarbonate and finally with water. Dry over magnesium sulfate and evaporate in vacuo to a residue comprising O-lanosteryl thiobenzoate. Purify by chromatographing on silica gel eluting with 3:1 light petroleum ether (60°–80° C) benzene. Combine the like fractions as determined by thin layer chromatography, evaporate the combined eluates in vacuo and recrystallize the resulting residue from ether/methanol, m.p. 187°–189° C.

C. O-Cholestanyl Thiobenzoate

In the procedure of Preparation 2A(1) by substituting cholestanol in place of cholesterol, there is obtained O-cholestanyl thiobenzoate.

PREPARATION 3

O-CHOLESTEROL-SUBSTITUTEDTHIOBENZOATE DERIVATIVES

A. O-Cholesteryl p-methoxythiobenzoate

In a manner similar to that described in Preparation 2A(1) treat N-(p-methoxybenzoyl)piperidine (2.65 gm.) with excess phosgene in dichloromethane at room temperature for 3 hours. Evaporate the reaction solution, then add a solution of cholesterol (3.86 gm.) in dichloromethane (20 ml.) and tetrahydorfuran (20 ml.) and stir the reaction mixture for 30 minutes at room temperature. Add 3 ml. of pyridine, then bubble dry hydrogen sulfide through the reaction mixture for 10 minutes and isolate the resultant product in a manner similar to that described in Preparation 2A(1) to obtain O-cholesteryl p-methoxythiobenzoate, yield 0.85 gm., 91%. Purify by recrystallizing from dichloromethane/ethanol; m.p. 190°–192° C.

Alternatively, the compound of this preparation may be prepared according to the procedure of Preparation 2B(2) utilizing thio-p-methoxybenzoylthioglycollic acid. Isolate and purify the resultant product in a manner similar to that described in Example 2B(2) to obtain O-cholesteryl p-methoxythiobenzoate.

B. O-Cholesteryl 2,4-dimethoxythiobenzoate

In a manner similar to that described in Preparation 3A, treat N,N-dimethyl-2,4-dimethoxybenzamide (2.8 gm.) with excess phosgene in dichloromethane at room temperature for 20 hours. Evaporate the reaction mixture, add cholesterol (3.86 gm.) in dichloromethane (20 ml.) and tetrahydrofuran (20 ml.) and stir at room temperature for 3 hours. Add 3 ml. of pyridine, then bubble dry hydrogen sulfide through the solution for 15 minutes and leave at room temperature for 15 hours. Isolate and purify the resultant product in a manner similar to that described to obtain O-cholesteryl 2,4-dimethoxy-thiobenzoate, m.p. 144°–146° C; $[\alpha]_D^{20}$ − 27.8 (c=5, chloroform); $\lambda_{max}$ 400, 329, 267, 243 nm ($\epsilon$=830, 10,400, 7,500 and 11,500). Combustion analysis: found: C, 76.4; H, 9.3; S, 5.7. $C_{36}H_{54}O_3S$ requires C, 76.3; H, 9.6, S, 5.7%.

C. O-Cholesteryl p-methoxysulfonylthiobenzoate

Add N,N-dimethyl-p-methylsulfonylbenzamide (2.4 gm.) to dichloromethane (20 ml.) containing phosgene (4 gm.) and allow the mixture to stand at room temperature for 2 days. Evaporate in vacuo. To the resultant residue add a solution of cholesterol (3.0 gm.) in dichloromethane (35 ml.) and hexamethylphosphoramide (5 ml.), and stir for 15 minutes. Add pyridine (3.5 ml.), stir for 15 minutes, then bubble anhydrous hydrogen sulfide through the reaction mixture for 10 minutes. Isolate the resultant product in a manner similar to that described in Preparation 3A to obtain O-cholesteryl p-methoxysulfonylthiobenzoate. Purify by recrystallization from benzene/ethanol; m.p. 235°–237° C; $[\alpha]_D^{23}$ − 32.3° (c=3.6, chloroform); $\lambda_{max}$ 426, 306 and 235 nm ($\epsilon$=220, 6,900 and 9,400); Combustion analysis: found: C, 71.7; H, 8.9; S, 10.7. $C_{35}H_{52}O_3S_2$ requires C, 71.9; H, 9.0; S, 11.0.

PREPARATION 4

S-METHYLXANTHATE DERIVATIVES OF CHOLESTEROL, LANOSTEROL AND ERGOSTEROL

A. O-Cholesteryl-S-methylxanthate

Stir at reflux temperature under an atmosphere of nitrogen for 3 hours a mixture of cholesterol (3.86 gm.), sodium hydride dispersion (80%, 0.5 gm.) and imidazole (20 mg.) in tetrahydrofuran (50 ml.). Add carbon disulfide (3 ml.) and continue heating at reflux temperature an additional 30 minutes; add methyl iodide (3 ml.), continue heating at reflux temperature for an additional 30 minutes. Add acetic acid (3 ml.) followed by water. Separate the layers and wash the aqueous layer with dichloromethane. Wash the combined organic extracts with dilute hydrochloric acid followed by aqueous sodium bicarbonate and finally with water. Dry over magnesium sulfate, evaporate in vacuo, dissolve the resultant residue in petroleum ether (40°–60° C)-benzene (1:1) and filter the solution down a small silica gel column. Evaporate the filtrate and recrystallize the resultant residue from ether/ethanol to obtain O-cholesteryl-S-methylxanthate; m.p. 126°–128° C; yield 92% theory.

B. Q-Lanosteryl-S-methylxanthate

Heat at reflux temperature for 20 hours a mixture of lanosterol (4.0 gm.), sodium hydride dispersion (80%, 0.75 gm.), imidazole (0.2 gm.), tetrahydrofuran (40 ml.), carbon disulfide (5 ml.) and hexamethylphosphoramide (5 ml.). Add dimethylsulfate (2 ml.), heat at reflux temperature for an additional 30 minutes, add acetic acid (2 ml.), then dilute with water, separate the layers and extract the aqueous layer with dichloromethane. Wash the combined organic extracts with dilute hydrochloric acid, then with sodium bicarbonate and finally with water. Dry over anhydrous magnesium sulfate and evaporate in vacuo to a residue comprising O-lanosteryl-S-methylxanthate. Purify by dissolving in petroleum ether/benzene (1:1), and passing the solution down a small silica gel column and recrystallizing twice the resultant residue from dichloromethane/methanol to give O-lanosteryl-S-methylxanthate; yield 9.3 gm., 85% theory; m.p. 124°–126° C; $[\alpha]_D^{20} + 129°$ (c=3, chloroform); $\lambda_{max}$ 354, 284 and 233 nm ($\epsilon$=77, 10,900 and 8,500); Combustion analysis: found: C, 74.2; H, 10.0; S, 12.2. $C_{32}H_{52}OS_2$ requires C, 74.4; H, 10.1; S, 12.4%.

C. O-Ergosteryl-S-methylxanthate

In a manner similar to that described in Preparation 4A treat ergosterol (4.1 gm.) in tetrahydrofuran with sodium iodide and imidazole followed by treatment with carbon disulfide, thence with methyl iodide and finally with acetic acid. Isolate the resultant product in a manner similar to that described to obtain O-ergosteryl-s-methylxanthate. Purify by chromatographing a petroleum either solution of the crude product in a manner similar to that described in Preparation 4A followed by recrystallization of the chromatographed product from ether/ethanol to give O-ergosteryl-S-methylxanthate; m.p. 144°–145° C (dec.); $[\alpha]_D^{20} - 52.1°$ (c=5, chloroform); $\lambda_{max}$ (cyclohexane) 292 sh 281 and 273 nm ($\epsilon$=6,500, 14,800 and 14,800); Combustion analysis: found: C, 74.2; H, 9.3; S, 13.2. $C_{30}H_{46}OS_2$ requires C, 74.0; H, 9.5; S, 13.2%.

PREPARATION 5

SELENOBENZOATE DERIVATIVES OF CHOLESTEROL, CHOLESTANOL, LANOSTEROL AND ERGOSTEROL

A. Q-Cholesteryl selenobenzoate

Add selenium powder (0.80 gm.) and sodium borohydride (0.50 gm.) to ethanol (40 ml.) and stir this mixture in an inert atmosphere until a clear, almost colorless, solution has formed (if necessary, add more sodium borohydride). Add acetic acid (0.4 ml.), cool the solution to 0° C and add a solution of O-cholesteryl-N,N-dimethylbenzimidinium chloride (5.5 gm.) in dichloromethane (40 ml.) and ethanol (10 ml.). Stir at room temperature for 30 minutes, dilute the mixture with dichloromethane (100 ml.), add water, separate the layers and wash the aqueous layer with dichloromethane. Wash the combined organic layer and extracts with dilute hydrochloric acid, aqueous sodium bicarbonate and finally with water. Dry over magnesium sulfate and evaporate the solution in vacuo. Recrystallize the resultant residue from dichloromethane/ethanol to give O-cholesteryl selenobenzoate; yield 4.3 gm. (78% theory); m.p. 160°–162° C; $\lambda_{max}$ 489, 337 and 257 nm ($\epsilon$=190, 8,800 and 9,400); Combustion analysis: found: C, 73.3; H, 9.2. $C_{34}H_{50}OSe$ requires C, 73.2; H, 9.3%.

B. In the procedure of Preparation 5A, substitute for O-cholesteryl-N,N-dimethylbenzimidinium chloride each of O-cholestanyl-N,N-dimethylbenzimidinium chloride, O-lanosteryl-N,N-dimethylbenzimidinium chloride and O-ergosteryl-N,N-dimethylbenzimidinium chloride (prepared from cholestanol, lanosterol and ergosterol in a manner similar to that described in Preparation 2A(2)) to obtain, respectively, O-cholestanyl selenobenzoate, O-lanosteryl selenobenzoate and O-ergosteryl selenobenzoate.

PREPARATION 6

MONO-O-THIOBENZOATE DERIVATIVES OF METHYL-4,6-O-BENZYLIDENE-α-D-GLUCOPYRANOSIDE

A. Methyl-4,6-O-Benzylidene-3-O-Thiobenzoyl-α-D-Glucopyranoside

Stir overnight a mixture comprising N,N-dimethylbenzamide (3.7 gm.) in dichloromethane (20 ml.) containing phosgene (4 gm.), evaporate in vacuo, add dichloromethane (20 ml.) to the resultant residue followed by a solution or pyridine (3.5 gm.) and methyl-4,6-O-benzylidene-α-D-glucopyranoside. (5.3 gm.) in dry tetrahydrofuran (15 ml.). Stir the mixture at room temperature for 30 minutes, then add dichloromethane (80 ml.) and pyridine (2.5 gm.) and bubble hydrogen sulfide through the reaction mixture for 10 minutes. Allow the mixture to stand at room temperature for 1 hour, then add water, separate the layers, extract the aqueous layer with dichloromethane, wash the combined organic layer and extracts with dilute hydrochloric acid followed by aqueous sodium bicarbonate and water; dry over sodium sulfate and evaporate in vacuo to a residue comprising a mixture of the 3-O-thiobenzoyl and the 2-O-thiobenzoyl of methyl-4,6-O-benzylidene-3-O-thiobenzoyl-α-D-glucopyranoside. Recrystallize from dichloromethane/peytroleum ether to give methyl-4,6-O-benzylidene-3-O-thiobenzoyl-glucopyranoside; 4.6g, m.p. 186°–187° C; $[\alpha]_D^{22} + 28.3$ (c=2, chloroform); $\lambda_{max}$ 411, 293, 253 nm ($\epsilon$=170, 11,400 and 8,000). Combustion analysis: found: C, 62.5; H, 5.5; S, 8.1. $C_{21}H_{22}O_6S$ requires C, 62.7; H, 5.5; S, 8.0%.

B. Methyl-4,6-O-Benzylidene-2-O-Thiobenzoyl-α-D-glucopyranoside

Chromatograph the filtrates from the crystallization of the 3-O-thiobenzoate (prepared as described in Preparation 6A), on silica gel eluting with benzene/ethyl acetate (20:1). Combine the like fractions containing the less polar 2-O-thiobenzoate ester as determined by thin layer chromatography and evaporate the combined eluates in vacuo to a residue comprising methyl-4,6-O-benzylidene-2-O-thiobenzoyl-α-D-glucopyranoside. Crystallize from dichloromethane/petroleum ether; m.p. 163°–164° C; $[\alpha]_D^{22} + 127°$; $\lambda_{max}$ 412, 294 and 252 nm ($\epsilon$=160, 10,800 and 8,200). Combustion analysis: found: C, 62.8; H, 5.3; S, 7.8. $C_{21}H_{22}O_6S$ requires C, 62.7; H, 5.5; S, 8.0%.

PREPARATION 7

TRANS-CYCLOHEXANE-1,2-DIOL-MONO-O-THIOBENZOATE AND TRANS-CYCLOHEXANE-1,2-DIOL-1-BENZOATE-2-O-THIOBENZOATE

Trans-cyclohexane-1,2-Diol-Mono-O-Thiobenzoate

In a manner similar to that described in Preparation 2A(1), add N,N-dimethylbenzamide (11 gm.) to phosgene in dichloromethane and allow the solution to stand at room temperature for 17 hours, then evaporate in vacuo. Dissolve the resultant residue in dichloromethane (75 ml.) and, with stirring add trans-1,2-cyclohexane-diol (7.5 gm.) in tetrahydrofuran (30 ml.) and dichloromethane (30 ml.). Add pyridine (15 ml.) dropwise and continue stirring the reaction mixture at room temperature for 30 minutes, then dilute the mixture with dichloromethane (100 ml.) and bubble hydrogen sulfide through the reaction mixture for 5 minutes. Continue stirring the reaction mixture for 2 hours, then dilute with water, separate the layers, extract the aqueous layer with dichloromethane, wash the combined organic layer and washes with hydrochloric acid, then add aqueous sodium bicarbonate and finally with water. Dry over magnesium sulfate, evaporate in vacuo and recrystallize the resultant residue from dichloromethane/petroleum ether to give trans-cyclohexane-1,2-diol mono-O-thiobenzoate; yield 12.1 gm. (80% theory); m.p. 104°–106° C; $\lambda_{max}$ 410, 286, 235 nm ($\epsilon$=170, 10,200 and 7,100); Combustion analysis: found: C, 65.9; H, 6.9; S, 13.4. $C_{13}H_{16}O_2S$ requires C, 66.1; H, 6.8; S, 13.6%.

B. Trans-cyclohexane-1,2-Diol 1-Benzoate 2-O-Thiobenzoate

Treat trans-cyclohexane-1,2-diol-monothiobenzoate with benzoyl chloride in pyridine at room temperature. Evaporate the reaction mixture and recrystallize the resultant residue from methanol to obtain trans-cyclohexane-1,2-diol 1-benzoate 2-O-thiobenzoate; m.p. 71°–73° C; $\lambda_{max}$ 412, 291, 281sh, 249 infl., 230.5 nm ($\epsilon$=170, 14,400, 13,600, 11,200 and 19,900). Combustion analysis: found: C, 70.5; H, 6.0; S, 9.45. $C_{20}H_{20}O_3S$ requires C, 70.6; H, 5.9; S, 9.4%.

PREPARATION 8

1,3,2',6'-TETRA-N-BENZYLOXYCARBONYL-2''-O-THIOBENZOYL-3'',4''-N,O-CARBONYLGENTAMICIN $C_2$

A. 1,3,2',6',3''-Penta-N-Benzyloxycarbonylgentamicin $C_2$

Stir vigorously in water (300 ml.) a mixture of gentamicin $C_2$ (30 gm.) and potassium carbonate (50 gm.) and add benzyl chloroformate (120 gm.) dropwise during a 2 hour period. Stir the reaction mixture overnight, separate the solid by filtration, wash with water then hexane. Dissolve the solid in chloroform (500 ml.), filter the solution over anhydrous sodium sulfate, concentrate to about 180 ml., then add the concentrated solution dropwise to a well-stirred mixture of ether (500 ml.) and hexane (2.5 liters). Separate the resultant precipitate by filtration, wash with hexane and dry at 60° C in vacuo to give 1,3,2',6',3''-penta-N-benzyloxycarbonylgentamicin $C_2$; yield 67.5 gm. (95% theory); m.p. 100°–102° C; $[\alpha]_D^{26}$ + 76.4° Chloroform, c=0.38).

B. 1,3,2'6'-Tetra-N-Benzyloxycarbonyl-3'',4''-N,O-Carbonylgentamicin $C_2$

To a solution of 1,3,2',6',3''-penta-N-benzyloxycarbonylgentamicin $C_2$ (30 gm.) in dry dimethylformamide (120 ml.) add hexane/washed sodium hydride (from 3 gm. of 50% dispersion). Stir the mixture at room temperature for 4 hours under an atmosphere of dry nitrogen. Add acetic acid (10 ml.) followed by methanol (20 ml.). Evaporate the like mixture to a small volume, add 200 ml. of chloroform to the resultant residue, wash the chloroform solution with 5% aqueous sodium bicarbonate (100 ml.), dry over sodium sulfate and concentrate to a volume of about 60 ml. Add the concentrated solution dropwise to a well-stirred mixture of ether (200 ml.) and hexane (800 ml.). Separate the resultant solid by filtration and dry at 60° C in vacuo to give 1,3,2',6'-tetra-N-benzyloxycarbonyl-3'',4''-N,O-carbonylgentamicin $C_2$; yield 25.5 gm. (93% theory); m.p. 93°–96° C; $[\alpha]_D^{26}$ + 66.2° (chloroform, c=0.43).

1,3,2',6'-Tetra-N-Benzyloxycarbonyl-2''-O-Thiobenzoyl-3'',4''-N,O-Carbonylgentamicin $C_2$ Add 1,3,2',6'-tetra-N-benzyloxycarbonyl-3'',4''-N,O-carbonylgentamicin $C_2$ (2 gm.) and N,N-dimethyl-α-chlorobenzimidinium chloride (1.5 gm.) to dry pyridine (3 ml.) and dichloromethane (4 ml.) and stir at room temperature for 18 hours. Dilute the solution with dichloromethane, bubble hydrogen sulfide gas through the solution for 10 minutes, allow the reaction mixture to stand at room temperature for 1 hour, then wash the solution with dilute hydrochloric acid then water, dry over sodium sulfate and evaporate to a residue comprising 1,3,2',6'-tetra-N-benzyloxycarbonyl-2''-O-thiobenzoyl-3'',4''-N,O-carbonylgentamicin $C_2$. Purify by chromatographing on silica gel eluting with 0.4% methanol/chloroform. Evaporate the combined eluates and dissolve the resultant residue in dichloromethane (10 ml.), add the solution to hexane (80 ml.), separate the resultant precipitate by filtration and dry at 60° C in vacuo to give purified 1,3,2',6'-tetra-N-benzyloxycarbonyl-2''-O-thiobenzoyl-3'',4''-N,O-carbonylgentamicin $C_2$; yield 1.65 gm. (74% theory); m.p. 121°–125° C; $[\alpha]_D^{26}$ + 119.9° (chloroform, c=0.61).

PREPARATION 9

1,3,2',6',3''-PENTA-N-BENZYLOXYCARBONYL-2''-O-THIOBENZOYLGENTAMICIN $C_2$

Add 1,3,2',6',3''-penta-N-benzyloxycarbonylgentamicin $C_2$ (1.4 gm.) and N,N-dimethyl-α-chlorobenzimidinium chloride (1.1 gm.) to dry pyridine (2 ml.) and dichloromethane (3.5 ml.) and stir overnight at room temperature. Dilute the solution with dichloromethane (25 ml.) and bubble hydrogen sulfide gas through the solution for 10 minutes. Allow the reaction mixture to stand at room temperature for 1 hour, then wash the solution with dilute hydrochloric acid, then water. Dry over sodium sulfate and evaporate to a residue comprising 1,3,2',6',3''-penta-N-benzyloxycarbonyl-2''-O-thiobenzoylgentamicin $C_2$. Purify by chromatographing on silica gel eluting with chloroform, then 1% methanol/chloroform, monitoring by thin layer chromatography (5% methanol/chloroform). Combine the like fractions of the desired product and evaporate the combined eluates in vacuo, dissolve the resultant residue in chloroform (6 ml.) and add the chloroform solution to stirred hexane (70 ml.). Separate the resultant product by filtration and dry at 60° C in vacuo to give purified 1,3,2',6',3''-penta-N-benzyloxycarbonyl-2''-O-thiobenzoylgentamicin; yield 1.27 gm.; (82% theory); m.p. 114°–118° C; $[\alpha]_D^{26}$ + 52.4° (chloroform, c=0.50).

PREPARATION 10

1,3,2',6',3''-PENTA-N-BENZYLOXYCARBONYL-2''-O-THIOBENZOYLSISOMICIN

Stir at room temperature for 16 hours a mixture of 1,3,2',6',3''-penta-N-benzyloxycarbonylsisomicin (6.0 gm.) and N,N-dimethyl-α-chlorobenzimidinium chloride (4.5 gm.) in dry pyridine (10 ml.) and dichloromethane (15 ml.). Add additional pyridine (10 ml.) and dichloromethane (100 ml.), bubble hydrogen sulfide gas through the solution until saturated (5 min.), then allow the reaction mixture to stand at room temperature for 3 hours. Wash the solution with 1 N hydrochloric acid, then water and finally with aqueous sodium bicarbonate. Dry the solution over sodium sulfate and evaporate to a residue. Chromatograph the resultant residue on a column of silica gel (400 gm.) containing sodium bicarbonate (10 gm.) eluting with chloroform containing 2% ethanol. Combine the like fractions containing the desired product as determined by thin layer chromatography, evaporate the combined fractions and precipitate the resultant residue from chloroform (15 ml.) into stirred n-hexane (200 ml.). Separate the resultant precipitate by filtration and dry at 60° C in vacuo to obtain 1,3,2′,6′,3″-penta-N-benzyloxycarbonyl-2″-O-thiobenzoylsisomicin; yield 2.89 gm. (41% theory); m.p. 95°–99° C; $[\alpha]_D^{26}$ + 75.6 (chloroform, c=0.47).

PREPARATION 11

1,3,2′,6′,3″-PENTA-N-ETHOXYCARBONYL-3′-O-THIOBENZOYL-2″-O-BENZOYL ANTIBIOTIC JI-20B AND 1,3,2′,6′,3″-PENTA-N-ETHOXYCARBONYL-4′-O-THIOBENZOYL-2″-O-BENZOYL ANTIBIOTIC JI-20B AND THE CORRESPONDING DERIVATIVES OF ANTIBIOTIC JI-20A

A. 1,3,2′,6′,3″(-penta-N-Ethoxycarbonyl-Antibiotic JI-20B and the Corresponding Penta-N-Ethoxycarbonyl-Antibiotic JI-20A (1) To a solution of Antibiotic JI-20B (20 gm.) in water (200 ml.) add with stirring sodium carbonate (60 gm.) followed by acetone (300 ml.). Cool the mixture to −5° C to 0° C, then add dropwise over a period of 2 hours a solution of ethyl chloroformate (108 gm.) in toluene (200 ml.). Allow the reaction mixture to gradually warm to room temperature and continue stirring for an additional 20 hours. Filter the reaction mixture and triturate the solids with acetone. Combine the acetone with the reaction mixture filtrate and concentrate in vacuo to a small volume. Extract the resulting aqueous residue thoroughly with chloroform, dry the combined chloroform extracts with sodium sulfate and evaporate in vacuo to a residue comprising 1,3,2′,6′,3″-penta-N-ethoxycarbonyl-Antibiotic JI-20B. Purify by dissolving in the residue a minimum volume of chloroform/methanol residue and chromatographing on a column of silica gel eluting with 6% methanol in chloroform. Monitor the fractions by thin layer chromatography and combine those containing 1,3,2′,6′,3″-penta-N-ethoxycarbonyl-Antibiotic JI-20B. Evaporate the combined eluates and dry the resulting solid at 50° C in vacuo; m.p. 155°–159° C; $[\alpha]_D^{26}$ + 95.1° (ethanol).

(2) In the above procedure, by utilizing as starting compound Antibiotic JI-20A there is obtained 1,3,2′,6′,3″-penta-N-ethoxycarbonyl-Antibiotic JI-20A.

1,3,2′,6′,3″-Penta-N-EThoxycarbonyl-3′,4′-O-Isopropylidene-Antibiotic JI-20B and the Corresponding Derivative of Antibiotic JI-20A (1) Suspend 1,3,2′,6′,3″-penta-N-ethoxycarbonyl-Antibiotic JI-20B (36.0 gm.) in benzene (650 ml.) and stir at reflux temperature for 3 hours with azeotropic distillation of traces of water. Remove the benzene in vacuo, dissolve the resultant residue in dry dimethylformamide (550 ml.) and add 2,2-dimethoxypropane (61 gm.) followed by p-toluenesulfonic acid (0.14 gm.). Heat the reaction mixture at 90° C for 1 hour, then reduce the volume of the reaction mixture by about ⅓ in vacuo, add additional 2,2-dimethoxypropane (43 gm.) and continue heating at 90° C for an additional 2 to 3 hours. Add 2 N ammonium hydroxide (6 ml.), then concentrate the reaction mixture in vacuo, dissolve the resultant residue in a minimum volume of chloroform/methanol and chromatograph on a column of silica gel eluting with 5% methanol in chloroform. Monitor the fractions by thin layer chromatography and combine those containing 1,3,2′,6′,3″-penta-N-ethoxycarbonyl-3′,4′-O-isopropylidene-Antibiotic JI-20B. Evaporate the combined eluates in vacuo to a residue comprising 1,3,2′,6′,3″-penta-N-ethoxycarbonyl-3′,4′-O-isopropylidene-Antibiotic JI-20B. Purify by rechromatographing in the same solvent system as described hereinabove, combining the like eluates as determined by thin layer chromatography and evaporating to a residue; m.p. 154°–156° C; $[\alpha]_D^{26}$ + 102.7° (ethanol). (2) In the above procedure, by utilizing as starting compound 1,3,2′,6′,3″-penta-N-ethoxycarbonyl-Antibiotic JI-20A, there is obtained 1,3,2′,6′,3″-penta-N-ethoxycarbonyl-3′,4′-O-isopropylidene-Antibiotic JI-20A.

C. 1,3,2′,6′,3″-Penta-N-Ethoxycarbonyl-3′,4′,-O-Isopropylidene-2″-O-Benzoyl-Antibiotic JI-20B and the Corresponding Derivative of Antibiotic JI-20A (1) Dissolve 1,3,2′,6′,3″-penta-N-ethoxycarbonyl-3′,4′-O-isopropylidene-Antibiotic JI-20B (55 gm.) in dry pyridine (500 ml.) and cool to −5° C to 0° C. Add benzoyl chloride (51 gm.) dropwise with stirring, then stir an additional 2 hours with gradual warming to 0° C. Evaporate the reaction mixture in vacuo, add chloroform to the resultant residue and extract the chloroform solution with saturated aqueous sodium bicarbonate solution. Dry the chloroform layer over sodium sulfate and evaporate in vacuo to a residue comprising 1,3,2′,6′,3″-penta-N-ethoxycarbonyl-3′,4′-O-isopropylidene-2″-O-benzoyl-Antibiotic JI-20B, which may be used without further purification in following Preparation 11D. To further purify, dissolve the foregoing residue in a minimum volume of chloroform/methanol and chromatograph on a column of silica gel eluting with 2% methanol in chloroform. Combine the like fractions containing the desired product as determined by thin layer chromatography, evaporate in vacuo and dry the resultant solid at 50° C in vacuo; $[\alpha]_D^{26}$ + 107.2° (ethanol). (2) In the above procedure, by utilizing as starting compound 1,3,2′,6′,3″-penta-N-ethoxycarbonyl-3′,4′-O-isopropylidene-Antibiotic JI-20A, there is obtained 1,3,2′,6′,3″-penta-N-ethoxycarbonyl-3′,4′-O-isopropylidene-2″-O-benzoyl-Antibiotic JI-20A.

D. 1,3,2′,6′,3″-Penta-N-Ethoxycarbonyl-2″-O-Benzoyl-Antibiotic JI-20B and the Corresponding Derivative of Antibiotic JI-20A (1) To a liter of 80% acetic acid cooled to approximately 5° C add 1,3,2′,6′,3″-penta-N-ethoxycarbonyl-3′,4′-O-isopropylidene-2″-O-benzoyl-Antibiotic JI-20B (62 gm.). Let the reaction mixture stir with gradual warming to room temperature over a period of 4 to 5 hours or until all the less polar isopropylidene derivative has been hydrolyzed as determined by thin layer chromatography. Evaporate the reaction mixture in vacuo, dissolve the resultant residue in a minimum volume of chloroform/methanol and chromatograph on silica gel eluting with 5% methanol in chloroform. Monitor the fractions by thin layer chromatography and combine those containing 1,3,2′,6′,3″-penta-N-ethoxycarbonyl-2″-O-benzoyl-Antibiotic JI-20B. Evaporate the combined eluates in vacuo and dry the resultant residue at 50° C in vacuo; m.p. 150°–155° C; $[\alpha]_D^{26}$ + 100.7° (ethanol).

(2) In the above procedure, by utilizing as starting compound 1,3,2′,6′,3″-penta-N-ethoxycarbonyl-3′,4′-O-isopropylidene-2″-O-benzoyl-Antibiotic JI-20B, there is obtained 1,3,2′,6′,3″-penta-N-ethoxycarbonyl-2″-O- benzoyl-Antibiotic JI-20A. E. (1) Stir at room temperature for 20 hours a solution of 1,3,2',6',3''-penta-N-ethoxycarbonyl-2''-O-benzoyl Antibiotic JI-20B (10.0 gm.) and N,N-dimethyl-α-chlorobenzimidinium chloride (4.0 gm.) in pyridine (20 ml.) and dichloromethane (60 ml.). Dilute the reaction mixture with dichloromethane (100 ml.), bubble dry hydrogen sulfide through the solution for 10 minutes and allow the reaction mixture to stand at room temperature for 2 hours. Wash the like solution with dilute hydrochloric acid then water, dry over sodium sulfate and evaporate to a residue comprising 1,3,2',6',3''-penta-N-ethoxycarbonyl-3'-O-thiobenzoyl-2''-O-benzoyl Antibiotic JI-20B and 1,3,2',6',3''-penta-N-ethoxycarbonyl-4'-O-thiobenzoyl-2''-O-benzoyl Antibiotic JI-20B. Separate the products by dissolving the foregoing residue in chloroform and apply the chloroform solution to a silica gel column (5 × 80 cm.) eluting first with chloroform (to remove N,N-dimethylthiobenzamide), then eluting with ethyl acetate/chloroform (1.5:1 by volume), monitoring by thin layer chromatographic analysis (silica gel/ethyl acetate). Combine the like fractions as determined by thin layer chromatography. Evaporate the combined less polar eluates and precipitate the resultant residue from dichloromethane (50 ml.) into hexane (600 ml.). Separate the resultant precipitate by filtration and dry at 60° C in vacuo to give 1,3,2',6',3''-penta-N-ethoxycarbonyl-3'-O-thiobenzoyl-2''-O-benzoyl Antibiotic JI-20B; yield 9.2 gm. (80% theory); m.p. 149°-154° C; $[\alpha]_D^{26}$ + 75° (chloroform, c=0.7).

Evaporate the combined like fractions containing the more polar product and purify the resultant residue by precipitation from chloroform (7 ml.) into hexane (100 ml.) and dry at 60° C in vacuo to give 1,3,2',6',3''-penta-N-ethoxycarbonyl-4'-O-thiobenzoyl-2''-O-benzoyl-Antibiotic JI-20B; yield 1.6 gm. (14% theory); m.p. 155°-160° C; $[\alpha]_D^{26}$ + 68.1° (chloroform, c=0.51). (2) In the above procedure, by utilizing as starting compound 1,3,2',6',3''-penta-N-ethoxycarbonyl-2''-O-benzoyl-Antibiotic JI-20A, there is obtained 1,3,2',6',3''-penta-N-ethoxycarbonyl-3'-O-thiobenzoyl-2''-O-benzoyl-Antibiotic JI-20A and 1,3,2',6',3''-penta-N-ethoxycarbonyl-4'-O-thiobenzoyl-2''-O-benzoyl-Antibiotic JI-20A.

PREPARATION 12

1,3,6',3''-TETRA-N-BENZYLOXYCARBONYL-3'-O-THIOBENZOYLGENTAMICIN B

Add N,N-dimethylbenzamide (0.75 gm.) to benzene (10 ml.) containing phosgene (1.2 gm.) and allow the solution to stand at room temperature overnight. Evaporate the solvent, add dichloromethane (20 ml.) to the resultant residue and to this solution with stirring add pyridine (2 ml.) and powdered 1,3,6',3''-tetra-N-benzyloxycarbonylgentamicin B (2.5 gm.). Stir at room temperature for 6 hours, add pyridine (2 ml.), then bubble dry hydrogen sulfide through the suspension for 2 minutes, add methanol (5 ml.), then bubble dry hydrogen sulfide through the solution for another 2 minutes. Allow the reaction mixture to stand at room temperature for 30 minutes, then pour the reaction mixture into water, add chloroform, separate the layers and extract the aqueous layer with chloroform. Wash the combined chloroform extracts with 1 N hydrochloric acid, saturated sodium bicarbonate, then water. Dry the chloroform solution over sodium sulfate and evaporate in vacuo. Chromatograph the resultant residue on silica gel (150 gm.) eluting with chloroform, then with 1.5% methanol/chloroform. Combine the like eluates containing the desired compound as determined by thin layer chromatography, evaporate the combined eluates in vacuo to a residue comprising 1,3,6',3''-tetra-N-benzyloxycarbonyl-3'-O-thiobenzoylgentamicin B. Purify by precipitation from chloroform (5 ml.) into hexane (50 ml.) and dry at 60° C in vacuo; yield 0.95 gm. (35% theory); m.p. 120°-124° C; $[\alpha]_D^{26}$ + 92.7° C (chloroform, c=0.35).

PREPARATION 13

1,3,2'-TRI-N-BENZYLOXYCARBONYL-5,6-O-CYCLOHEXYLIDENE-3''-O-THIOBENZOYL-4',6'-O,N-CARBONYLNEAMINE

A. 1,3,2',6'-Tetra-N-Benzyloxycarbonyl-5,6-O-Cyclohexylideneneamine

To a solution of 1,3,2',6'-tetra-N-benzyloxycarbonylneamine (10.0 gm., 11.7 mM) in N,N-dimethylformamide (100 ml.) add cyclohexanone dimethyl acetal (10 ml.) and P-toluenesulfonic acid (200 mg.), and heat at 50° C in vacuo at a pressure of 20 mm. of mercury for 16 hours. Bring the reaction mixture to atmospheric pressure, add 5 ml. of methanol and heat at 45° C for 3.5 hours, then add sodium bicarbonate (1 gm.) and evaporate in vacuo at 60° C/0.5 mm. of mercury. Triturate the resultant residue with water (250 ml.), separate the resultant solid by filtration, wash with water and dry at 50° C/15 mm. of mercury. Purify the resultant dry solid by triturating with about 50 ml. of ether and separating the resultant precipitate by filtration to obtain 1,3,2',6'-tetra-N-benzyloxycarbonyl-5,6-O-cyclohexylideneneamine, yield 8.5 gm. $\lambda_{max}^{nujol}$: 3.0 (NH, O-H), 5.8, 5.9 (C=O). nmr: (CDCl$_3$–CD$_3$OD) (1:1): 1.50 (cyclohexylidene), 7.30 δ (Cbz).

B. 1,3,2'-Tri-N-Benzyloxycarbonyl-5,6-O-Cyclohexylidene-4',6'-O,N-Carbonylneamine Wash a suspension of 1.36 gm. (28.4 mM) of 50% sodium hydride (in mineral oil) with hexane under argon. Repeat this procedure a second time, then add dimethylformamide (28 ml.) followed by 1,3,2',6'-tetra-N-benzyloxycarbonyl-5,6-O-cyclohexylideneneamine (13.3 gm.) in one portion. Stir the reaction mixture under an atmosphere of argon at room temperature for 90 minutes, then pour into cold water (300 ml.). Separate the resultant precipitate by filtration, triturate the solid with ether and dry to obtain 1,3,2'-tri-N-benzyloxycarbonyl-5,6-O-cyclohexylidene-4',6'-O,N-carbonylneamine, yield 7.83 gm. (66% theory). $\lambda_{max}^{nujol}$: 5.80, 5.85, 5.90 μ (oxazinone, Cbz C=O). nmr: (CDCl$_3$–CD$_3$OD 3:1) 7.22 (15H, Cbz); 4.0–5.40 (φCH$_2$-O and C$_1$H, 7H); 1.54 δ (cyclohexylidyl H).

This product was used without further purification in following Preparation 13C.

C. 1,3,2'-Tri-N-Benzyloxycarbonyl-5,6-O-Cyclohexylidene-3'-O-Thiobenzoyl-4',6'-O,N-Carbonylneamine Dissolve N,N-dimethylbenzamide (7.05 gm.) in 10% phosgene in dry methylene chloride (94 ml.). Stir overnight under an atmosphere of argon, evaporate in vacuo and dissolve the resultant residue in dry methylene chloride (40 ml.). Add a solution of 1,3,2',6'-tetra-N-benzyloxycarbonyl-5,6-O-cyclohexylidene-4',6'-O,N-carbonylneamine (7.83 gm.) in dry tetrahydrofuran (42 ml.) and dry triethylamine (8.9 ml.). Stir the reaction mixture under an atmosphere of argon for 4.5 hours, then add dry methylene chloride (ca 25 ml.) and triethylamine (ca 12.5 ml.). Bubble hydrogen sulfide gas through the solution for about 15 minutes, then add dry tetrahydrofuran (20 ml.) and continue bubbling hydrogen sulfide through the solution for an additional 15 minutes. After the addition of hydrogen sulfide, stir the reaction mixture for 45 minutes, then pour the reaction mixture into aqueous sodium chloride. Add ethyl acetate, separate the layers and extract the aqueous layer with ethyl acetate. Wash the combined ethyl acetate extracts with 1 N hydrogen chloride, saturated aqueous sodium bicarbonate, then water. Dry the ethyl acetate solution over sodium sulfate and evaporate in vacuo. Triturate the resultant residue with ether, filter and chromatograph the resultant residue on silica gel (a 1 kg. column) developing with 60% ethyl acetate/chloroform, then with ethyl acetate and combine the like eluates containing the desired compound as determined by thin layer chromatography. Evaporate the combined eluates in vacuo to a residue comprising 1,3,2'-tri-N-benzyloxycarbonyl-5,6-O-cyclohexylidene-3'-O-thiobenzoyl-4',6'-O,N-carbonylneamine, yield 2.2 gm.; $\lambda_{max}^{nujol}$: 2.95, 3.05 (NH, OH); 5.80 (oxazinone); 5.85, 5.90 (Cbz C=O); 6.45, 6.60 (arom.); 8.30 (C=S); 13.20, 13.60, 14.40 μ (arom.). $\lambda_{max}^{MeOH}$: 2.92 (ε:7700); 2.52 and 2.56 mμ (ε:5150). NMR: (CDCl$_3$–CD$_3$OD, 3:1); 8.13 (d. of d J$_1$ =8 Hz, J$_2$=2Hz S=C–φ, 2H); 7.40, 7.33, 7.83 (Cbz, Bz 18H), 4.75-5.50 (7H, φ-CH$_2$–O, C$_1$ H); 1.56 δ (cyclohexylidyl).

PREPARATION 14

SELENOBENZOATE INTERMEDIATES

A. 1,3,2',6',3"-Penta-N-Benzyloxycarbonyl-2"-O-Selenobenzoyl Derivatives of Gentamicin C$_2$ and Sisomicin (1) In a manner similar to that described in Preparation 9 stir a mixture of 1,3,2',6',3"-penta-N-benzyloxycarbonylgentamicin C$_2$ and N,N-dimethyl-α-chlorobenzimidinium chloride in pyridine and dichloromethane overnight at room temperature. Dilute the solution with dichloromethane, then add this solution at 0° C to a solution of sodium hydrogen selenide in ethanol prepared from selenide powder and sodium borohydride in the manner described in Preparation 5A. Stir the reaction mixture at room temperature for 30 minutes, dilute with dichloromethane, add water, separate the layers and wash the aqueous layer with dichloromethane. Wash the combined organic layer and extracts with dilute hydrochloric acid, aqueous sodium bicarbonate and finally with water. Dry over sodium sulfate and evaporate to a residue comprising 1,3,2',6',3"-penta-N-benzyloxycarbonyl-2"-O-selenobenzoylgentamicin C$_2$. Purify via column chromatography on silica gel in a manner similar to that described in Preparation 9 for the purification of the 2"-O-thiobenzoyl derivative.

(2) In the procedure of Preparation 14A(1) by utilizing as starting compound 1,3,2',6',3"-penta-N-benzyloxycarbonylsisomicin there is obtained 1,3,2',6',3"-penta-N-benzyloxycarbonyl-2"-O-selenobenzoylsisomicin.

B. 1,3,2',6',3"-Penta-N-Ethoxycarbonyl-3'-O-Selenobenzoyl-2"-O-Benzoyl-Antibiotic JI-20B and 1,3,2',6',3"-Penta-N-Ethoxycarbonyl-4'-O-Selenobenzoyl-2"-O-Benzoyl-Antibiotic JI-20B and the Corresponding Derivatives of Antibiotic JI-20A (1) In a manner similar to that described in Preparation 11E treat 1,3,2',6',3"-penta-N-ethoxycarbonyl-2"-O-benzoyl-Antibiotic JI-20B with N,N-dimethyl-α-chlorobenzimidinium chloride in pyridine and dichloromethane. Dilute the reaction mixture with dichloromethane and add to a solution of sodium hydrogen selenide in ethanol prepared by reaction of selenium powder and sodium borohydride in the manner described in Preparation 5A. Stir the reaction mixture at room temperature for 2 hours, wash the solution with dilute hydrochloric acid, then water, dry over sodium sulfate and evaporate to a residue comprising 1,3,2',6',3"-penta-N-ethoxycarbonyl-3'-O-selenobenzoyl-2"-O-benzoyl-Antibiotic JI-20B and 1,3,2',6',3"-penta-N-ethoxycarbonyl-4'-O-selenobenzoyl-2"-O-benzoyl-Antibiotic JI-20B. Separate and purify each of the products by dissolving the product mixture in chloroform and chromatographing on silica gel column in a manner similar to that described in Preparation 11E.

(2) In a manner smilar to that described in Preparation 14B(1) treat 1,3,2',6',3"-penta-N-ethoxycarbonyl-2"-O-benzoyl-Antibiotic JI-20A with N,N-dimethyl-α-chlorobenzimidinium chloride in pyridine and dichloromethane, followed by treatment of the intermediate thereby formed with sodium hydrogen selenide. Isolate and purify the resultant products in a manner similar to that described in Preparation 14B(1) to obtain 1,3,2',6',3"-penta-N-ethoxycarbonyl-3'-O-selenobenzoyl-2"-O-benzoyl-Antibiotic JI-20A and 1,3,2',6',3"-penta-N-ethoxycarbonyl-4'-O-selenobenzoyl-2"-O-benzoyl-Antibiotic JI-20A.

C. 1,3,2'-Tri-N-Benzyloxycarbonyl-5,6-O-Cyclohexylidene-3'-O-Selenobenzoyl-4',6'-O,N-Carbonylneamine In a manner similar to that described in Preparation 13C treat a solution of 1,3,2',6'-tetra-N-benzyloxycarbonyl-5,6-O-cyclohexylidene-4',6'-O,N-carbonylneamine in tetrahydrofuran and triethylamine with N,N-dimethyl-α-chlorobenzimidinium chloride in methylene chloride. After stirring the reaction mixture under an atmosphere of argon for 4.5 hours, add the reaction mixture to a solution of sodium hydrogen selenide prepared as described in Preparation 5A continuing stirring the reaction mixture for about an hour and add water, separate the layer and wash the aqueous layer with dichloromethane. Wash the combined organic layer and extracts with dry hydrochloric acid, aqueous sodium bicarbonate and finally with water. Dry over magnesium sulfate and evaporate the solution in vacuo. Purify the resultant residue on silica gel via chromatography in a manner similar to that described in Preparation 13C to obtain 1,3,2'-tri-N-benzyloxycarbonyl-5,6-O-cyclohexylidene-3'-O-selenobenzoyl-4',6'-O,N-carbonylneamine.

PREPARATION 15

1,3,2'-TRI-N-ETHOXYCARBONYL-5,6,4',6'-DI-O-ISOPROPYLIDENE-3'-O-THIOBENZOYL-PAROMAMINE

A. 1,3,2'-Tri-N-Ethoxycarbonylparomamine (1) To a stirred solution of paromamine (20 gm.) and potassium carbonate (20 gm.) in water (200 ml.) and ethanol (150 ml.), add dropwise ethyl chloroformate (30 ml.) and stir at room temperature for an hour. Dilute with water (300 ml.) then heat the mixture to reflux temperature, adjust the pH to about 8 to 9 by adding small portions of sodium bicarbonate, then add small portions of ethanol to the refluxing reaction mixture until a clear solution is obtained. Cool at 0° to 5° C overnight, separate the resultant precipitate by filtration, wash with water, and dry in vacuo at 100° C to give 1,3,2'-tri-N-ethoxycarbonylparomamine.

(2) Additional product is obtained from the filtrate by evaporating it in vacuo to dryness, extracting the resultant residue with ethanol, evaporating the filtrate and crystallizing the resultant residue from a minimum volume of 1:1 ethanol/water. Total yield 25.5 gm. (77% theory); m.p. 270°–275° C (dec.); $[\alpha]_D^{26}$ + 80.2° (dimethylformamide, c=0.44).

B. 1,3,2'-Tri-N-Ethoxycarbonyl-5,6;4',6'-Di-O-IsopropylideneParomamine

To a solution of 1,3,2'-tri-N-ethoxycarbonylparomamine (7.5 gm.) and p-toluenesulfonic acid (0.25 gm.) in dry dimethylformamide (70 ml.), add 2,2-dimethoxypropane (20 ml.) and stir the solution at 100°–110° C for 1 hour. Evaporate the solution in vacuo to a volume of about 60 ml., add an additional 7 ml. of 2,2-dimethoxypropane and heat the solution at 110° C for an additional 1.5 hours. Add triethylamine (2 ml.) and evaporate the solution in vacuo. Dissolve the resultant residue in chloroform (150 ml.), wash with water (2 × 150 ml.), separate the layers, dry the organic phase over sodium sulfate and evaporate. Chromatograph the resultant residue on silica gel eluting with chloroform containing 2% methanol. Combine the like eluates containing the desired product as determined by thin layer chromatography and evaporate. Dry the resultant residue at 60° C/1 mm. Hg to obtain 1,3,2'-tri-N-ethoxycarbonyl-5,6;4',6'-di-O-isopropylideneparomamine; yield 7.4 gm. (80% theory); m.p. 139°–142° C; $[\alpha]_D^{26}$ +42.2° (chloroform, c=0.4).

C. 1,3,2'-Tri-N-Ethoxycarbonyl-5,6;4',6'-Di-O-Isopropylidene-3'-O-Thiobenzoylparomamine Add N,N-dimethylbenzamide (3 gm.) to benzene (50 ml.) containing phosgene (5 gm.) and keep the resultant mixture at room temperature for 48 hours. Evaporate the solvent in vacuo, add dry dichloromethane (40 ml.) and to the resulting solution with stirring add di-isopropylethylamine (8.5 ml.), then add 1,3,2'-tri-N-ethoxycarbonyl-5,6;4',6'-di-O-isopropylideneparomamine (7.5 gm.). Stir the resulting reaction solution at room temperature for 6 hours, dilute with chloroform (50 ml.), then bubble dry hydrogen sulfide through the solution for 5 minutes, then allow to stand at room temperature for 40 minutes. Wash the solution with water (2 × 150 ml.), dry over potassium carbonate, filter, evaporate and chromatograph the resultant residue on silica gel (250 gm.) eluting with chloroform, then with 1% methanol in chloroform. Evaporate the like eluates containing the desired product as determined by thin layer chromatography, dissolve the resultant residue in chloroform (20 ml.) and add the chloroform solution dropwise to stirred hexane (400 ml.). Separate the resultant precipitate by filtration and dry in vacuo at 60° C to give 1,3,2'-tri-N-ethoxycarbonyl-5,6;4',6'-di-O-isopropylidene-3'-O-thiobenzoylparomamine; yield 8.4 gm. (94% theory); m.p. 133°–136° C; $[\alpha]_D^{26}$ +8.6° (chloroform, c=0.44).

PREPARATION 16

DIOL THIOCARBONATE DERIVATIVES

A. O-Methyl-O-3β-Cholestanyl Thiocarbonate

To a solution of N-(3β-cholestanyloxythiocarbonyl)imidazole (5.0 gms.) in dry dichloromethane (25 ml.) add triethyloxonium fluoroborate (1.95 gms.). Stir at room temperature for one hour, then add dropwise at 0° C a solution of sodium (0.23 gms.) in anhydrous methanol (10 ml.) over a 10 minute period. Stir at room temperature for an additional 10 minutes, then add chloroform and wash the organic solution with dilute hydrochloric acid, then with water. Dry the solution over sodium sulfate, evaporate, and chromatograph the resultant residue on silica gel eluting with hexane/benzene (1:1). Combine the like eluates of the desired product as determined by thin layer chromatography, evaporate, and recrystallize the resultant residue from ether to obtain O-methyl-O-3β-cholestanylthiocarbonate as colorless crystals.

B. 1,3,2',6',3"-Penta-N-Ethoxycarbonyl-3',4'-O,O-Thiocarbonyl-2"-O-Benzoyl-Antibiotic JI-20B and the corresponding derivative of antibiotic JI-20A (1) To a stirred refluxing solution of 1,3,2',6',3"-penta-N-ethoxycarbonyl-2"-O-benzoyl-Antibiotic JI-20B (5 gms.) in dry tetrahydrofuran (30 ml.), add dropwise over a period of two hours a solution of N,N'-thiocarbonyldiimidazole (0.95 gms.) in dry tetrahydrofuran (10 ml.). Continue heating the reaction mixture at reflux temperature for 20 hours, then evaporate in vacuo and chromatograph the resultant residue on silica gel eluting with chloroform containing 2% methanol. Combine the like fractions containing the desired product as determined by thin layer chromatography and evaporate to a residue comprising 1,3,2',6',3"-penta-N-ethoxycarbonyl-3',4'-O,O-thiocarbonyl-2"-O-benzoyl-Antibiotic JI-20B.

(2) Treat 1,3,2',6',3"-penta-N-ethoxycarbonyl-2"-O-benzoyl-Antibiotic JI-20A in the manner described above to obtain 1,3,2',6',3"-penta-N-ethoxycarbonyl-3',4'-O,O-thiocarbonyl-2"-O-benzoyl-Antibiotic JI-20A.

C. Adenosine-5'-O-Acetyl-2',3'-Thiocarbonate (1) Adenosine-2',3'-Thiocarbonate

Dissolve adenosine (1.23 gms.) in dry dimethylacetamide (25 ml.) and add bis(imidazole-1-yl)trione (1.0 gms.). Heat the mixture at reflux temperature (for 4 hours) under an atmosphere of nitrogen, then evaporate. Wash the resultant solid residue repeatedly with tetrahydrofuran, then recrystallize from methanol:water to give adenosine-2',3'-thiocarbonate; yield 1.0 gms.; m.p. 201°–205° C; $[\alpha]_D^{22}$ −43° (methanol, c=1.0).

(2) Adenosine-5'-O-Acetyl-2',3'-Thiocarbonate

To a solution of adenosine-2',3'-thiocarbonate (0.9 gms.) in dry pyridine (25 ml.) at 0° C add slowly acetic anhydride (0.4 ml.). Stir the reaction mixture for 16 hours at room temperature, dilute with ether, wash the ether solution with water, dry over sodium sulfate and evaporate in vacuo. Crystallize the resultant residue from methanol:water to obtain adenosine-5'-O-acetyl-2',3'-thiocarbonate as yellow needles; yield 0.780 gms.; m.p. 164°–169° C; $[\alpha]_D^{22}$ −39° (methanol, c=0.9).

D. 1,2-O-Isopropylidene-3-O-Methyl-5,6-O-Thiocarbonyl-α-D-glucofuranose 1,2-O-Isopropylidene-3-O-methyl-α-D-glucofuranose (10.1 gms.) (prepared by methylation with sodium hydride-methyl iodide in tetrahydrofuran followed by selective acidic hydrolysis) was dissolved in tetrahydrofuran (90 ml.) and N,N'-thiocarbonyldiimidazole (8.40 gms.) was added. The mixture was refluxed for 30 minutes under nitrogen and then evaporated. The solid residue was dissolved in dichloromethane (400 ml.), washed with cold hydrochloric acid (50 ml., 2 N) and cold water (10 ml.), and dried (MgSO$_4$). Evaporation and crystallization yielded the compound of this example, m.p. 111.5°–112° (from ethyl acetate-light petroleum).

EXAMPLE 1

PREPARATION OF 5α-CHOLESTANE

A. To a solution of tri-n-butylstannane (450 mg.) in toluene (20 ml.) under an atmosphere of argon and at reflux temperature, add over a period of 30 minutes a solution of O-cholestanyl thiobenzoate (510 mg.) in toluene (25 ml.). Heat at reflux temperature until the solution is almost colorless (1.5 hours). Remove the solvent in vacuo to obtain a residue comprising a mixture of 5α-cholestane and S-(tri-n-butylstannyl)thiobenzoate. Chromatograph the crude residue on alumina (Grade I) eluting with petroleum ether (b.p. 60°–80° C). Combine the eluates and evaporate in vacuo to a residue comprising 5α-cholestane. Purify by recrystallizing from acetone/methanol; yield 270 mg. (73%); m.p. 78.5°–79.5° C.

B. In the above procedure of Example IA, use N-(3β-cholestanyloxythiocarbonyl)imidazole (510 mg.) as starting material instead of O-cholestanyl thiobenzoate. Isolate and purify the resultant product in a manner similar to that described to obtain 5α-cholestane; yield 79% theory.

EXAMPLE 2

PREPARATION OF 5-CHOLESTENE

A. From the Thioimidazolide Intermediate

In a manner similar to that described in Example 1A(1) treat N-(3β-cholesteryloxythiocarbonyl)imidazole (505 mg.) with tri-n-butylstannane in toluene. Isolate and purify the resultant product in a manner similar to that described to obtain 5-cholestene; yield 278 mg. (74% theory); m.p. 92°–93.5° C (from ethanol).

B. From the S-Methylxanthate Intermediate

In a manner similar to that described in Example 2A, add over a 1 hour period a solution of O-cholesteryl-S-methylxanthate (1.0 gm.) in toluene (30 ml.) to a stirred solution of tri-n-butylstannane (800 mg.) in toluene (30 ml.) at reflux temperature under an atmosphere of argon. Continue heating the reaction mixture at reflux temperature for 6 hours, then evaporate in vacuo and chromatograph the resultant residue in a manner similar to that described in Example 1A(1) to give 5-cholestene; m.p. 90°–92° C; yield 78%.

C. From the Thiobenzoate and Substituted Thiobenzoate Intermediates

In a manner similar to that described in Example 1A(1) add O-cholesteryl thiobenzoate (2 mmoles) in toluene (35 ml.) over a period of one hour to tri-n-butylstannane (3 mmoles) in toluene (30 ml.) at reflux temperature under an atmosphere of argon. Heat the reaction mixture at reflux temperature until almost colorless. Isolate and purify the resultant product in a manner similar to that described in Example 1A(1) to obtain 5-cholestene.

In similar manner treat each of O-cholesteryl-p-methoxythiobenzoate, O-cholesteryl-2,4-dimethoxy thiobenzoate, O-cholesteryl-p-methoxysulfonyl thiobenzoate in toluene with tri-n-butylstannane at reflux temperature under an atmosphere of argon. In each case, isolate and purify each of the resultant products in a manner similar to that described in Example 1A(1) to obtain 5-cholestene.

EXAMPLE 3

8,24-LANOSTADIENE

To a stirred solution of tri-n-butylstannane (1.2 gm.) in xylene (30 ml.) at reflux temperature and under argon, add during a 30 minute period a solution of O-lanosteryl-S-methylxanthate (1.4 gm.) in xylene (40 ml.). Continue heating the reaction mixture at reflux temperature for 2 hours, then evaporate the reaction mixture and chromatograph the resultant residue on alumina (Grade I) eluting with petroleum ether. Evaporate the eluates to a residue comprising 8,24-lanostadiene. Further purify by recrystallizing from acetone; m.p. 79°–80° C; yield 83% theory.

EXAMPLE 4

5,7,22-ERGOSTATRIENE

Treat O-ergosteryl-S-methylxanthate (0.95 gm.) with tri-n-butylstannane (0.65 gm.) in toluene (60 ml.) in a manner similar to that described in Example 3. Isolate the resultant product via chromatography in a manner similar to that described to obtain 5,17,22-ergostatriene. Purify by recrystallization from ethanol; yield 0.52 gm. (67% theory); m.p. 111°–112.5° C; $[\alpha]_D^{22}$ −99.5 (c=2, chloroform); Combustion analysis; found: C, 88.1; H, 11.4. $C_{28}H_{44}$ requires C, 88.35; H, 11.65%.

EXAMPLE 5

3-DEOXY-1,2,5,6-DI-O-ISOPROPYLIDENE-α-D-GLUCOFURANOSE

A. 1,2,5,6-Di-O-Isopropylidene-α-D-Glucofuranose-3-O-(S-methylxanthate)

In a manner similar to that described in Preparation 4A, treat 1,2,5,6-di-O-isopropylidene-α-D-glucofuranose in tetrahydrofuran under an atmosphere of nitrogen with sodium hydride and imidazole followed by treatment with carbon disulfide followed by iodomethane. Isolate the resultant product in a manner similar to that described to obtain 1,2,5,6-di-O-isopropylidene-α-D-glucofuranose-3-O-(S-methylxanthate).

B. 3-Deoxy-1,2,5,6-Di-O-Isopropylidene-α-D-Glucofuranose

Dissolve 1,2,5,6-di-O-isopropylidene-3-O-α-D-glucofuranose-(S-methylxanthate) (1.75 gm.) in toluene (40 ml.); add over a period of one hour to a solution of tri-n-butylstannane (2.1 gm.) in toluene (30 ml.) at reflux temperature under an atmosphere of argon. Continue heating the reaction mixture at reflux temperature (about 18 hours), then remove the solvent at 50° C in vacuo. Chromatograph the resultant residue on silica gel eluting with petroleum ether (b.p. 40°–60° C) containing increasing proportions of ether (5% increments). Combine the like eluates containing the desired 3-deoxy compound as determined by thin layer chromatography and evaporate the combined eluates in vacuo to a residue comprising 3-deoxy-1,2,5,6-di-O-isopropylidene-α-D-glucofuranose as a colorless oil; yield 1.04 gm. (85% theory); $[\alpha]_D^{20}$ −7.5 (c=10, chloroform).

EXAMPLE 6

1,6-ANHYDRO-2-DEOXY-3,4-ISOPROPYLIDENE-D-GALACTOSE

A. 1,6-Anhydro-3,4-O-Isopropylidene-β-D-Galactose-2-O-(S-Methylxanthate)

In a manner similar to that described in Preparation 4A, stir a mixture of 1,6-anhydro-3,4-O-isopropylidene-β-D-galactose (900 mg.), sodium hydride dispersion (80%, 270 mg.), imidazole (5 mg.) and dry tetrahydrofuran (12 ml.) under an atmosphere of nitrogen for 30 minutes at room temperature. Add carbon disulfide (2 ml.), stir for another hour, add methyl iodide (2 ml.), stir for another hour, then add acetic acid (2 ml.). Dilute the reaction mixture with water, separate the layers and extract the aqueous layer with dichloromethane. Wash the combined organic layer and extracts with dilute hydrochloric acid followed by aqueous sodium bicarbonate, then water. Dry over anhydrous magnesium sulfate and evaporate in vacuo to a residue comprising 1,6-anhydro-3,4-O-isopropylidene-β-D-galactose-2-O-(S-methylxanthate).

B. 1,6-Anhydro-2-Deoxy-3,4-O-Isopropylidene-D-Galactose

To a solution of 1,6-anhydro-3,4-O-isopropylidene-β-D-galactose-2-O-(S-methylxanthate) (prepared in Example 6A) in toluene (40 ml.) at reflux temperature under an atmosphere of argon, add over a period of 1 hour a solution of tri-n-butylstannane (1.6 gm.) in toluene (30 ml.). Continue heating at reflux temperature for 16 hours, then evaporate the reaction mixture in vacuo and chromatograph the resultant residue on silica gel eluting with petroleum ether (40°–60° C) containing increasing portions of ether (5% increments). Combine the like fractions containing the desired 2-deoxy compound as determined by thin layer chromatography and evaporate the combined fractions in vacuo to a residue comprising 1,6-anhydro-2-deoxy-3,4-isopropylidene-D-galactose; yield 780 mg. (94% theory). Purify further by distillation, b.p. 75° C at 2 mm.; $[\alpha]_D^{22}$ −141° (c=3.5, chloroform); Combustion analysis: found: C, 57.9; H, 7.5. $C_9H_{14}O_4$ requires C, 58.05; H, 7.6%.

EXAMPLE 7

1,6-ANHYDRO-2-DEOXY-3,4-O-ISOPROPYLIDENE-D-ALTROSE

In the procedure of Examples 6A and 6B utilize as starting compound 1,6-anhydro-3,4-O-isopropylidene-β-D-altrose (900 mg.) to obtain 1,6-anhydro-2-deoxy-3,4-O-isopropylidene-D-altrose (710 mg., 86% theory); b.p. 83° at 4 mm; $[\alpha]_D^{22}$ −123° (c=5, chloroform); Combustion analysis: found: C, 57.8; H, 7.5. $C_9H_{14}O_4$ requires C, 58.05; H, 7.6.

EXAMPLE 8

METHYL-4,6-O-BENZYLIDENE-3-DEOXY-α-D-GLUCOPYRANOSIDE

In a manner similar to that described in Example 1A(1), add a solution of methyl-4,6-O-benzylidene-3-O-thiobenzoyl-α-D-glucopyranoside (0.8 gm.) in toluene (50 ml.) over a 1 hour period to a solution of tri-n-butylstannane (0.65 gm.) in toluene (30 ml.) at reflux temperature under an atmosphere of argon. Heat at reflux temperature until the solution is almost colorless, then evaporate in vacuo and chromatograph the resultant residue on alumina (Grade III) eluting with 10–30% benzene followed by an ethyl acetate/benzene mixture. Combine the like eluates containing the desired 3-deoxy product as determined by thin layer chromatography. Evaporate the combined eluates in vacuo to a residue comprising methyl-4,6-O-benzylidene-3-deoxy-α-D-glucopyranoside. Further purify by crystallization from petroleum ether/chloroform; yield 70% theory; m.p. 184°–186° C; $[\alpha]_D^{20}$ +123°.

EXAMPLE 9

METHYL-4,6-O-BENZYLIDENE-2-DEOXY-α-D-GLUCOPYRANOSIDE

Subject methyl-4,6-O-benzylidene-2-O-thiobenzoyl-gluco-D-pyranoside to the procedure described in above Example 8 and isolate and purify the resultant product in a manner similar to that described therein to obtain methyl-4,6-O-benzylidene-2-deoxy-α-D-glucopyranoside.

EXAMPLE 10

METHYL-4,6-O-BENZYLIDENE-2,3-DIDEOXY-α-D-GLUCOPYRANOSIDE

A. Methyl-4,6-O-Benzylidene-3-Deoxy-2-Q-Thiobenzoyl-α-D-Glucopyranoside

In a manner similar to that described in Preparation 6A, stir overnight a mixture of N,N-dimethylbenzamide in dichloromethane containing phosgene. Evaporate in vacuo, then dissolve the resultant residue in dichloromethane and to this solution, with stirring, add pyridine followed by methyl-4,6-O-benzylidene-3-deoxy-α-D-glucopyranoside in dry tetrahydrofuran. Continue stirring at room temperature for 30 minutes, then to the methyl-4,6-O-benzylidene-3-deoxy-2-O-(N,N-dimethylbenzimidinium chloride)-α-D-glucopyranoside intermediate thereby formed, add dichloromethane and pyridine. Bubble hydrogen sulfide gas through the reaction mixture for 10 minutes. Continue stirring the reaction mixture for 1 hour at room temperature, then add water, separate the layers, wash the aqueous layer with dichloromethane, wash the combined organic layer and extracts with hydrochloric acid followed by aqueous sodium bicarbonate and finally with water. Dry over magnesium sulfate and evaporate in vacuo to a residue comprising methyl-4,6-O-benzylidene-2-O-thiobenzoyl-3-deoxy-α-D-glucopyranoside.

B. Methyl-4,6-O-Benzylidene-2,3-Dideoxy-α-D-Glucopyranoside

In a manner similar to that described in Example 8, treat methyl-4,6-O-benzylidene-2-O-thiobenzoyl-3-deoxy-α-D-glucopyranoside with tri-n-butylstannane in toluene under an atmosphere of argon. Isolate and purify the resultant product in a manner similar to that described to obtain methyl-4,6-O-benzylidene-2,3-dideoxy-α-D-glucopyranoside.

Treat methyl-4,6-O-benzylidene-2-deoxy-α-D-glucopyranoside in a manner similar to that described in above Example 10A to obtain methyl-4,6-O-benzylidene-2-deoxy-3-O-thiobenzoyl-α-D-glucopyranoside which, upon treatment with tri-n-butylstannane in toluene under an atmosphere of argon in the manner described in Example 10B, yields methyl-4,6-O-benzylidene-2,3-dideoxy-α-D-glucopyranoside.

EXAMPLE 11

CYCLOHEXYL BENZOATE

To a stirred solution of tri-n-butylstannane (1.2 gm.) in toluene at reflux temperature and under an atmosphere of argon add over a period of 30 minutes a solution of 1,2-cyclohexane-diolbenzoate-O-thiobenzoate (0.95 gm.) in toluene (30 ml.). Heat at reflux temperature until the solution is almost colorless (about 2 hours), then evaporate in vacuo and chromatograph the resultant residue on silica gel eluting with petroleum ether (b.p. 60°-80° C)/ benzene (1:1). Evaporate the combined eluates in vacuo to a residue comprising cyclohexylbenzoate. Purify by distillation, b.p. 120° C at 0.5 mm; yield 280 mg. (51% theory).

EXAMPLE 12

CYCLOHEXANOL

In a manner similar to that described in Example 11 treat 1,2-cyclohexanediol mono-thiobenzoate with tri-n-butylstannane in toluene under an atmosphere of nitrogen. Isolate and purify the resultant product in a manner similar to that described in Example 11 to obtain cyclohexanol.

EXAMPLE 13

2''-DEOXYGENTAMICIN $C_2$

A. 1,3,2',6',3''-Penta-N-Benzyloxycarbonyl-2''-Deoxygentamicin $C_2$

To a stirred solution of tri-n-butylstannane (2.0 gm.) in dry toluene (100 ml.) at reflux temperature under an atmosphere of argon add dropwise over a 30 minute period a solution of 1,3,2',6',3''-penta-N-benzyloxycarbonyl-2''-O-thiobenzoylgentamicin $C_2$ (3.0 gm.) in toluene (100 ml.). Continue refluxing until the solution is decolorized (2.5 hours), then evaporate the solution and chromatograph the resultant residue on silica gel eluting with 0.25% methanol/chloroform. Combine the like fractions containing the desired product as determined by thin layer chromatography and evaporate the combined eluates in vacuo to a residue comprising 1,3,2',6',3''-penta-N-benzyloxycarbonyl-2''-deoxygentamicin $C_2$; yield 1.92 gm. (72% theory); m.p. 92°-95° C; $[\alpha]_D^{26}$ +65.7° (chloroform, c=0.48). Combustion analysis: found: C, 63.4; H, 6.3; N, 6.1. $C_{60}H_{71}N_5O_{16} \cdot H_2O$ requires C, 63.4; H, 6.5; N, 6.2%.

B. 2''-Deoxygentamicin $C_2$

Hydrogenate at 60 psi for 48 hours a solution of 1,3,2',6',3''-penta-N-benzyloxycarbonyl-2''-deoxygentamicin $C_2$ (0.5 gm.) in dioxane (30 ml.) and 0.1 N hydrochloric acid (7 ml.) in the presence of 10% palladium on charcoal (0.25 gm.). Remove the catalyst by filtration, wash with water, and evaporate the filtrate. Dissolve the resultant residue in water (10 ml.) and treat with IRA-401S resin (OH$^-$form) until the pH is about 9-10. Remove the resin by filtration and wash with water. Evaporate the combined filtrate and washes and chromatograph the resultant residue on a short silica gel column eluting with the lower phase of a 2:1:1 chloroform:methanol-concentrated ammonium hydroxide mixture. Combine the like fractions as determined by thin layer chromatography containing the desired product, evaporate the combined fractions in vacuo, dissolve the resultant residue in water (2 ml.) and pass through a short column of IRA-401S (OH$^-$) resin. Collect the eluates under an atmosphere of nitrogen and lyophilize the combined eluates to a residue comprising 2''-deoxygentamicin $C_2$ (0.150 gm.) (72% theory). Alternatively, the compound of this example is prepared according to the procedure outlined in Example 13C.

C. 1,3,2',6'-Tetra-N-Benzyloxycarbonyl-3'',4''-N,O-Carbonyl-2''-Deoxygentamicin $C_2$ To a solution of 1,3,2',6'-tetra-N-benzyloxycarbonyl-2''-O-thiobenzoyl-3'',4''-N,O-carbonylgentamicin $C_2$ (1.5 gm.) in dry toluene (100 ml.) add tri-n-butylstannane (1.0 gm.) and heat the reaction mixture at reflux temperature under an atmosphere of argon until the solution is decolorized (about 3 hours). Evaporate the solvent, wash the resultant residue by decantation with several portions to obtain 1,3,2',6'-tetra-N-benzyloxycarbonyl-3'',4''-N,O-carbonyl-2''-deoxygentamicin $C_2$.

Dissolve the foregoing product in dry tetrahydrofuran (5 ml.) and add to a stirred solution of sodium (2gm.) in liquid ammonia (50 ml.). Continue stirring for 20 minutes, then add 10 ml. of methanol and allow the ammonia to evaporate. Dilute the resultant residue with water (25 ml.) and heat the solution at reflux temperature under an atmosphere of nitrogen for 20 hours, cool, stir the solution with IRC-50 (H$^+$) resin until all the aminoglycoside is adsorbed onto the resin as determined by thin layer chromatographic analysis on the aqueous layer. Pour the resin into a column, wash the column with water, then elute the resin with 1 N aqueous ammonia. Combine the like eluates containing the desired product as determined by thin layer chromatography and evaporate the combined eluates to a residue comprising a mixture of 2''-deoxygentamicin $C_2$ together with gentamicin $C_2$. Chromatograph the mixture on silica gel (50 gm.) eluting with the lower phase of a 2:1:1 chloroform:methanol:concentrated ammonium hydroxide system. Evaporate the combined eluates containing the desired product as determined by thin layer chromatography, dissolve the resultant residue in water and pass through IRA-401S (OH$^-$) resin. Lyophilize the combined eluates to a residue comprising 2''-deoxygentamicin $C_2$; yield 0.195 gm. (43% theory).

EXAMPLE 14

2''-DEOXYSISOMICIN

A. 1,3,2', 6'-Tetra-N-Benzyloxycarbonyl-2''-Deoxysisomicin

Dissolve 1,3,2',6'-tetra-N-benzyloxycarbonyl-2''-O-thiobenzoylsisomicin (2.2 gm.) in toluene (65 ml.) and add dropwise during a 30 minute period to a stirred solution of tri-n-butylstannane (1.4 gm.) in toluene (45 ml.) at reflux temperature under an atmosphere of argon. Continue heating the reaction mixture at reflux temperature for 18 hours, then cool and add to stirred hexane (600 ml.). Separate the resultant precipitate by filtration and dry in vacuo to give 1,3,2',6', 3''-penta-N-benzyloxycarbonyl-2''-deoxysisomicin, which is used without further purification in the following Example 14B.

B. 2''-Deoxysisomicin

Dissolve the 1,3,2',6',3''-penta-N-benzyloxycarbonyl-2''-deoxysisomicin prepared in Example 14A in dimethylsulfoxide (20 ml.). Add potassium hydroxide (3 gm.) in water (4 ml.) and stir the solution at room temperature for 72 hours. Dilute with water (50 ml.), stir the aqueous solution with IRC-50 (H$^+$) resin until all the aminoglycoside has been adsorbed onto the resin. Pour the resin into a column, wash the resin with water, then elute with 2 N ammonium hydroxide. Combine the like eluates containing the desired product as determined by thin layer chromatography and evaporate the combined eluates to a residue comprising a mixture of 2''-deoxysisomicin and sisomicin. Purify further by chromatographing on silica gel eluting with a solvent mixture comprising chloroform:methanol:ammonium hydroxide (5%) (1:2:1 volume). Combine the less polar fractions, evaporate the combined fractions, add water to the resultant residue and pass through IRA-401S (OH$^-$) resin, wash the resin with water and lyophilize the combined aqueous fractions to a residue comprising 2—''- deoxysisomicin; yield 0.228 (33% theory); m.p. 91°–95° C; $[\alpha]_D^{26}$ + 139.1° (water, c=0.48). pmr (D$_2$O): δ 1.21 (s, 3,4″—CH$_3$); 2.34 (s, 3,3″N—CH$_3$); 3.15 (s, broad, 2, H$_6$′); 4.02 (d, J$_{5eq5ax}$ = 12.5Hz, 1, H$_{5eq}$); 4.88 (m, 1, H$_4$′); 5.24 (m, 1, H$_1$″) and 5.35 (d, J$_{1',2'}$=2.5Hz, 1, H$_1$′). Mass Spectrum: m/e 431, 346, 334, 316, 306, 288, 163, 144, 127. Combustion analysis: found: C, 51.0; H, 8.55; N, 15.2. C$_{19}$N$_{37}$N$_5$O$_6$. H$_2$O requires C, 50.8; H, 8.7; N, 15.6.

EXAMPLE 15

3′-DEOXY-ANTIBIOTIC JI-20B AND 3′-DEOXY-ANTIBIOTIC JI-20A

A. 1,3,2′,6′,3″-Penta-N-Ethoxycarbonyl-2″-O-Benzoyl-3′-Deoxy-Antibiotic JI-20B

To a stirred solution of tri-n-butylstannane (3.0 gm.) in toluene (50 ml.) at reflux temperature under an atmosphere of argon add dropwise during a period of 1.5 hours a solution of 1,3,2′,6′,3″-penta-N-ethoxycarbonyl-3′-O-thiobenzoyl-2″-O-benzoyl Antibiotic JI-20B (3.5 gm.) in dry toluene (100 ml.). Continue stirring the reaction mixture at reflux temperature until the solution becomes colorless (about 30 minutes to 1 hour). Evaporate the solution and chromatograph the resultant residue on silica gel eluting with ethyl acetate. Combine the like fractions containing the desired compound as determined by thin layer chromatography and evaporate the combined eluates in vacuo. Dissolve the resultant residue in chloroform (15 ml.) and add the chloroform solution to stirred hexane (200 ml.). Separate the resultant precipitate by filtration and dry at 60° C in vacuo to give 1,3,2′,6′,3″-penta-N-ethoxycarbonyl-2″-O-benzoyl-3′-deoxy Antibiotic JI-20B; yield 2.20 gm. (71% theory); m.p. 127°–132° C; $[\alpha]_D^{26}$ + 65.5° (chloroform, c=0.91).

B. 3′-Deoxy Antibiotic JI-20B

To a solution of 1,3,2′,6′,3″-penta-N-ethoxycarbonyl-2″-O-benzoyl-3′-deoxy Antibiotic JI-20B (0.88 gm.) in dimethylsulfoxide (15 ml.) add potassium hydroxide (1.7 gm.) in water (2 ml.) and stir the reaction mixture for 20 hours under an atmosphere of argon. Add water (10 ml.) and stir the reaction mixture at reflux temperature under an atmosphere of argon for 45 hours. Dilute the reaction mixture with water, adsorb the aminoglycoside onto IRC-50 (H$^+$) resin. Pour the resin into a column, wash with water then elute with 1 N ammonium hydroxide. Combine the like fractions containing the desired product as determined by thin layer chromatography and evaporate the combined eluates and chromatograph the resultant residue on silica gel eluting with chloroform/methanol/7% ammonium hydroxide (1:2:1) mixture. Combine the like eluates containing the desired product as determined by thin layer chromatography, evaporate the combined eluates, dissolve the resultant residue in water and pour the aqueous solution through IRA-401S (OH$^-$) resin. Lyophilize the aqueous eluate to a residue comprising 3′-deoxy Antibiotic JI-20B.

C. 3′-Deoxy-Antibiotic JI-20A

By subjecting Antibiotic JI-20A to the series of reactions outlined in above Examples 15A and 15B, there is obtained 3′-deoxy-Antibiotic JI-20A.

EXAMPLE 16

4′-DEOXY ANTIBIOTIC JI-20B AND 4′-DEOXY ANTIBIOTIC JI-20A

A. 1,3,2′,6′,3″-Penta-N-Ethoxycarbonyl-2″-O-Benzoyl-4′-Deoxy Antibiotic JI-20B and 1,3,2′,6′,3″-Penta-N-Ethoxycarbonyl-2″-O-Benzoyl-4′-Deoxy Antibiotic JI-20A (1) To a stirred solution of tri-n-butylstannane (1.70 gm.) in toluene (80 ml.) at reflux temperature under an atmosphere of argon add dropwise during a period of 45 minutes a solution of 1,3,2′,6′,3″-penta-N-ethoxycarbonyl-4′-O-thiobenzoyl-2″-O-benzoyl Antibiotic JI-20B (1.50 gm.) in toluene (50 ml.). Continue stirring the reaction mixture at reflux temperature for 2 hours, evaporate the solution and chromatograph the resultant residue on silica gel eluting with ethyl acetate. Combine the like fractions containing the desired product as determined by thin layer chromatography and dissolve the resultant residue in chloroform (7 ml.), add the chloroform solution to stirred hexane (100 ml.), separate the resultant precipitate by filtration and dry at 60° C in vacuo to give 1,3,2′,6′,3″-penta-N-ethoxycarbonyl-2″-O-benzoyl-4′-deoxy Antibiotic JI-20B; yield 1.12 gm. (80% theory); m.p. 137°–140° C; $[\alpha]_D^{26}$ + 83° (chloroform, c=0.44).

(2) Treat 1,3,2′,6′,3″-penta-N-ethoxycarbonyl-4′-O-thiobenzoyl-2″-O-benzoyl Antibiotic JI-20A with tri-n-butylstannane in toluene in the manner described hereinabove to obtain 1,3,2′,6′,3″-penta-N-ethoxycarbonyl-2″-O-benzoyl-4′-deoxy Antibiotic JI-20A.

B. 4′-Deoxy Antibiotic JI-20B and 4′-Deoxy Antibiotic JI-20A (1) In a manner similar to that described in Example 15B treat 1,3,2′,6′,3″-penta-N-ethoxycarbonyl-2″-O-benzoyl-4′-deoxy Antibiotic JI-20B (0.88 gm.) in dimethylsulfoxide (15 ml.) with potassium hydroxide (1.7 gm.) in water (2 ml.). Isolate and purify the resultant product in a manner similar to that described in Example 15C to obtain 4′-deoxy Antibiotic JI-20B; yield 0.28 gm. (62% theory); m.p. 100°–110° $[\alpha]_D^{26}$ + 153.4 (water, c=0.5 ). pmr (100 MHz in D$_2$O): δ 1.05 (d, J$_{6',7'}$=7Hz; 3, H$_7$′); 1.20 (s, 3, 4″-CH$_3$); 2.55 (d, J$_{2'',3''}$=12.5Hz, 1, H$_3$″); 2.51 (s, 3, 3″-NCH$_3$); 3.79 (dd, J$_{1'',2''}$=4Hz, J$_{2'',3''}$=12.5Hz, 1, H$_2$″); 4.05 (d, J$_{5''eq,5''ax}$=12Hz, 1, 5eq); 5.08 (d, J$_{1'',2''}$=4Hz, 1, H$_1$″) and 5.35 (d, J$_{1'',2''}$=4Hz, 1, H$_1$″). Mass Spectrum m/e 480, 362, 350, 349, 332, 322, 304, 191, 173, 163, 160, 136, 135, 118.

(2) In similar manner treat 1,3,2′,6′,3″-penta-N-ethoxycarbonyl-2″-O-benzoyl-4′-deoxy Antibiotic JI-20A with aqueous potassium hydroxide to obtain 4′-deoxy Antibiotic JI-20A.

EXMAPLE 17

3′-DEOXYGENTAMICIN B

To a stirred solution at reflux temperature of tri-N-butylstannane (0.6 gm.) in toluene (12 ml.) under an atmosphere of argon add dropwise over a 30 minute period a solution of 1,3,6′,3″-tetra-N-benzyloxycarbonyl-3′-O-thiobenzoylgentamicin B (0.7 gm.) in toluene (20 ml.). Continue refluxing for an additional hour, remove the solvent in vacuo to a residue comprising 1,3,6′,3″-tetra-N-benzyloxycarbonyl-3′-deoxygentamicin B. Dissolve the residue in dry tetrahydrofuran (3 ml.) and add to a stirred solution of sodium (1 gm.) in liquid ammonia (40 ml.). Stir for 15 minutes, then cautiously add methanol (10 ml.) followed by water (50 ml.). Evaporate the solution in vacuo to a volume of about 30 ml. Adsorb the aminoglycosides onto IRC-50 (H$^{30}$) resin, wash with water and elute with 1 N ammonium hydroxide, combine the like fractions containing the aminoglycoside as determined by thin layer chromatography, evaporate the combined eluates and chromatograph the resultant residue on silica gel eluting with chloroform/methanol/concentrated ammonium hydroxide (2:1:0.25 by volume). Combine the like fractions containing the desired product as determined by thin layer chromatography, evaporate the combined fractions, dissolve the resultant residue in water (1 ml.) and pass down a column of IRA-401S (OH$^{31}$) resin, eluting with water. Collect the eluate under nitrogen and lyophilize to a residue comprising 3'-deoxygentamicin B; yield 0.06 gm.; $[\alpha]_D^{26}$ + 157° (water, c=0.44).

EXAMPLE 18

3'-DEOXYNEAMINE

A. 1,3,2'-Tri-N-Benzyloxycarbonyl-5,6-O-Cyclohexylidene-3'Deoxy-4',6'-O,N-Carbonylneamine To a refluxing solution of tri-n-butylstannane (2.8 ml.) in toluene (20 ml.) add dropwise over a period of 20 minutes a solution of 1,3,2'-tri-N-benzyloxycarbonyl-5,6-o-cyclohexylidene-3'-O-thiobenzoyl-4',6'-O,N-carbonylneamine (1.0 gm.) in toluene (80 ml.) heated to just below its boiling point. After the addition is completed, heat the reaction mixture at reflux temperature for an additional 20 minutes, then evaporate in vacuo, triturate the resultant residue with ether and filter the resultant precipitate comprising 1,3,2'-tri-N-benzyloxycarbonyl-5,6-o-cyclohexylidene-3'-deoxy-4',6'-O,N-carbonylneamine, yield 875 mg.; $\lambda_{mas}^{nujol}$: 5.80, 5.90, 5.95 (oxazinone and Cbz C=O. NMR: (CDCl$_3$-CD$_3$OD 3:1); 7.38 (Cbz, 15H); 4.90-5.30 ($\phi$-CH$_2$-O, C$_1$-H); 1.57 $\delta$ (cyclohexylidyl).

This compound is used without further purification in the procedure of Example 18B.

B. 5,6-O-Cyclohexylidene-3'-Deoxyneamine

Dissolve 1,3,2'-tri-N-benzyloxycarbonyl-5,6-o-cyclohexylidene-3'-deoxy-4',6'-O,N-carbonylneamine (240 mg.) in 2 N sodium hydroxide (50 ml.) and dioxane (6 ml.). Heat the solution at reflux temperature for 18 hours, cool to room temperature and add to a column of BioRex 70 (H$^+$form) resin (120 ml.). Wash the column first with water, then elute with 1.5 N ammonium hydroxide. Combine the like fractions containing the desired product as determined by thin layer chromatography and evaporate in vacuo to a residue comprising 5,6-O-Cyclohexylidene-3'-deoxyneamine, yield 68 mg.; NMR: (D$_2$O, ext. TMS): 5.8 (C$_1$-H); 1.7 $\delta$ (cyclohexylidyl).

This compound is used without further purification in the procedure of Example 18C.

C. 3'-Deoxyneamine (1) Dissolve the 5,6-O-cyclohexylidene-3'-deoxyneamine prepared in Example 18B in glacial acetic acid (10 ml.) and water (10 ml.). Heat at 80°-85° C for 8 hours, then evaporate in vacuo. Dissolve the resultant residue in water and pass the aqueous solution through IRA (Amberlite) 401S resin (OH$^-$form) (20 ml.). Evaporate the combined eluates to a residue comprising 3'-deoxyneamine, yield 16 mg.

(2) Alternatively, 3'-deoxyneamine is obtained from the compound of Example 18A by the following procedures of Examples 18D and 18E.

D. 1,3,2'-Tri-N-Benzyloxycarbonyl-3'-Deoxy-4',6'-O,N-Carbonylneamine

Dissolve 1,3,2'-tri-N-benzyloxycarbonyl-5,6-o-cyclohexylidene -3'-deoxy-4',6'-O,N-carbonylneamine (887 mg.) in 80% acetic acid (45 ml.) and stir at room temperature for 22 hours. Evaporate the reaction mixture in vacuo, triturate with chloroform (10 ml.) and filter the resultant solid comprising 1,3,2'-tri-N-benzyloxycarbonyl-3'-deoxy-4',6'-O,N-carbonylneamine, yield 558 mg.; $\lambda_{max}^{nujol}$: 5.80, 5.90, 5.95 (oxazinone, Cbz C=O).

This compound is used without further purification in the procedure of Example 18E.

E. 3'-Deoxyneamine

In a manner similar to that described in Example 18B, treat 1,3,2'-tri-N-benzyloxycarbonyl-3'-deoxy-4',6'O,N-carbonylneamine with 2 N sodium hydroxide in dioxane. Isolate and purify the resultant product in a manner similar to that described to obtain 3'-deoxyneamine.

EXAMPLE 19

DEOXYGENATION BY TREATING SELENOBENZOATE ESTERS WITH TRI-N-BUTYLSTANNANE

A. 5-Cholestene

Dissolve O-cholesteryl selenobenzoate (1.12 gm.) and tri-n-butylstannane (0.9 gm., 1.5 equivalents) in dry toluene (75 ml.) and heat at reflux temperature under an atmosphere of argon until the solution is decolorized (approximately 1 hour). Evaporate the solution in vacuo and chromatograph the resultant residue on alumina (activity=I) eluting with hexane. Evaporate the combined eluates and crystallize the resultant residue from acetone/methanol to obtain 5-cholestene, yield 0.34 gm. (47% theory).

B. 2'-Deoxygentamicin C$_2$ (1) 1,3,2',6',3''-Penta-N-Benzyloxycarbonyl-2''-Deoxygentamicin C$_2$ Treat a solution of 1,3,2',6',3''-penta-N-benzyloxycarbonyl-2''-O-selenobenzoylgentamicin C$_2$ in toluene with a solution of tri-n-butylstannane in toluene at reflux temperature under an atmosphere of argon in a manner similar to that described in Example 13A. Isolate and purify the resultant product in a manner similar to that described to obtain 1,3,2',6',3''-penta-N-benzyloxycarbonyl-2''-deoxygentamicin C$_2$.

(2) Hydrogenate the 1,3,2',6',3''-penta-N-benzyloxycarbonyl-2''-deoxygentamicin C$_2$ in dioxane in the presence of 10% palladium on charcoal in a manner similar to that described in Example 13B to obtain 2''-deoxygentamicin C$_2$.

C. 2''-Deoxysisomicin (1) In a manner similar to that described in Example 14A treat 1,3,2',6'-tetra-N-benzyloxycarbonyl-2''-O-selenobenzoylsisomicin in toluene with tri-n-butylstannane at reflux temperature under an atmosphere of argon. Isolate the resultant product in a manner similar to that described to obtain 1,3,2',6',3''-penta-N-benzyloxycarbonyl-2''-deoxysisomicin.

(2) Treat 1,3,2',6',3''-penta-N-benzyloxycarbonyl-2''-deoxysisomicin in dimethylsulfoxide with aqueous potassium hydroxide in the manner described in Example 14B. Isolate and purify the resultant product in a manner similar to that described to obtain 2''-deoxysisomicin.

D. 3'-Deoxy-Antibiotic JI-20B and 3'-Deoxy-Antibiotic JI-20A (1) In a manner similar to that described in Example 15A add dropwise during a period of 1.5 hours a solution of 1,3,2',6',3''-penta-N-ethoxycarbonyl-3'-O-selenobenzoyl-2''-O-benzoyl-Antibiotic JI-20B in toluene to a stirred solution of tri-n-butylstannane in toluene at reflux temperature under an atmosphere of argon.

Isolate and purify the resultant product in a manner similar to that described to obtain 1,3,2',6',3''-penta-n-ethoxycarbonyl-2''-O-benzoyl-3'-deoxy-Antibiotic JI-20B.

(2) In a manner similar to that described in Example 15B treat 1,3,2',6',3''-penta-N-ethoxycarbonyl-2''-O-benzoyl-3'-deoxy-Antibiotic JI-20B in dimethylsulfoxide with aqueous potassium hydroxide. Isolate and purify the resultant product in a manner similar to that to obtain 3'-deoxy-Antibiotic JI-20B.

(3) By subjecting 1,3,2',6',3''-penta-N-ethoxycarbonyl-3'-O-selenobenzoyl-2''-O-benzoyl-Antibiotic JI-20A to the procedure described in above Examples 19D(1) and 19D(2) there is obtained 3'-deoxy-Antibiotic JI-20A.

E. 4'-Deoxy-Antibiotic JI-20B and 4'-Deoxy-Antibiotic JI-20A (1) In a manner similar to that described in Example 16A(1) treat 1,3,2',6',3''-penta-N-ethoxycarbonyl-4'-O-selenobenzoyl-2''-O-benzoyl-Antibiotic JI-20B in toluene with tri-n-butylstannane in toluene under an atmosphere of nitrogen. Isolate and purify the resultant product in a manner similar to that described to obtain 1,3,2',6'3''-penta-N-ethoxycarbonyl-2''-O-benzoyl-4'deoxy-Antibiotic JI-20B.

(2) In a manner similar to that described in Example 15B treat 1,3,2',6',3''-penta-N-ethoxycarbonyl-2''-O-benzoyl-4'-deoxy-Antibiotic JI-20B in dimethylsulfoxide with aqueous potassium hydroxide. Isolate and purify the resultant product in a manner similar to that described to obtain 4'-deoxy-Antibiotic JI-20B.

(3) In similar manner treat 1,3,2',6',3''-penta-N-ethoxycarbonyl-4'-O-thiobenzoyl-2''-O-benzoyl-Antibiotic JI-20A with tri-n-butylstannane in toluene to obtain 1,3,2',6',3''-penta-N-ethoxycarbonyl-2''-O-benzoyl-4'-deoxy-Antibiotic KI-20A. Treat the foregoing with aqeuous potassium hydroxide in dimethylsulfoxide to obtain 4'-deoxy-Antibiotic JI-20A.

F. 3'-Deoxyneamine (1) In a manner similar to that described in Example 18A to a refluxing solution of tri-n-butylstannane in toluene add dropwise a solution of 1,3,2'-tri-N-benzyloxycarbonyl-5,6-o-cyclohexylidene-3'-O-selenobenzoyl-4',6'-O,N-carbonylneamine. Isolate the resultant product in a manner similar to that described to obtain 1,3,2'-tri-N-benzyloxycarbonyl-5,6-O-cyclohexylidene-3'-deoxy-4',6'-O,N-carbonylneamine.

(2) In a manner similar to that described in Example 18B treat 1,3,2'-tri-N-benzyloxycarbonyl-5,6-O-cyclohexylidene-3'-deoxy-4',6'-O,N-carbonylneamine with sodium hydroxide and dioxane. Isolate and purify the resultant product in a manner similar to that described to obtain 5,6-O-cyclohexylidene-3'-deoxyneamine.

(3) In a manner similar to that described in Example 18C(1) treat 5,6-O-cyclohexylidene-3'-deoxyneamine in aqueous glacial acetic acid. Isolate the resultant product in a manner similar to that described to obtain 3'-deoxyneamine.

EXAMPLE 20

3'-DEOXYPAROMAMINE

A. 1,3,2'-Tir-N-Ethoxycarbonyl-3'-Deoxyparomamine

Add a solution of 1,3,2'-tri-N-ethoxycarbonyl-5,6;4',6'-di-O-isopropylidene-3'-O-thiobenzoylparomamine (7 gm.) in toluene (100 ml.) dropwise during a 60 minute period to a refluxing solution of tri-n-butylstannane (6 gm.) in toluene (200 ml.) under an atmosphere of argon. Continue heating the reaction solution at reflux temperature for another hour, evaporate the solution, dissolve the resultant residue in chloroform (20 ml.) and add the solution slowly to stirred hexane (500 ml.). Separate the resultant precipitate by filtration and dry in vacuo to give 1,3,2'-tri-N-carbethoxy-5,6;4',6'-di-O-isopropylidene-3'-deoxyparomamine. Add the precipitate in acetic acid (90 ml.) in water (20 ml.) and heat at 50° C until dissolved. Keep the solution at room temperature for 18 hours, then evaporate in vacuo. Recrystallize the resultant residue from aqueous ethanol and dry the resultant precipitate in vacuo at 60° C to obtain 1,3,2'-tri-N-ethoxycarbonyl-3'-deoxyparomamine; yield 2.72 gm. (51% theory); m.p. 270–273° C (dec.); $[\alpha]_D^{26} + 65.9°$ (Dimethylformamide, c=0.42).

B. 3'-Deoxyparomamine

In a manner similar to that described in Example 15B treat 1,3,2'-tri-N-ethoxycarbonyl-3'-deoxyparomamine with potassium hydroxide in water and isolate the resultant product in a manner similar to that described. Purify by chromatography on silica gel eluting with a solvent mixture comprising chloroform/methanol/concentrated ammonium hydroxide (3:4:1 by volume). Combine the like fractions containing the desired compound as determined by thin layer chromatography, evaporate the combined fractions, dissolve the resultant residue in water and pass down IRA-401S (OH⁻) resin eluting with water. Lyophilize the eluate to a residue of 3'-deoxyparomamine; $[\alpha]_D^{26} = 103.3°$ (water, c=0.61).

EXAMPLE 21

DEOXYGENATION OF DIOL THIOCARBONATE DERIVATIVES

A. 5α-Cholestane

Dissolve O-methyl-O-3β-cholestanyl thiocarbonate (2.0 gms.) and tri-n-butylstannane (2.0 gms.) in dry toluene (25 ml.) then, at reflux temperature and under an atmosphere of argon, add dropwise over a period of one hour a solution of azobisisobutyronitrile (0.2 gms.) in toluene (5 ml.). Add additional tri-n-butylstannane (1.0 gm.) followed by additional azobisisobutyronitrile (0.2 gms.) in toluene (5 ml.) over a period of an hour. Continue heating the reaction mixture at reflux temperature under an atmosphere of argon with periodic small additions of tri-n-butylstannane and axobisisobutyronitrile until there is no starting compound present as determined by thin layer chromatography. Evaporate the reaction mixture, dissolve the resultant residue in hexane, pass the hexane solution through a column of alumina (activity=1) eluting with hexane. Combine like fractions containing the product as determined by thin layer chromatography and evaporate, then recrystallize the resultant residue to obtain 5α-cholestane.

B. 3'-Deoxy-Antibiotic JI-20B and 4'-Deoxy-Antibiotic JI-20B

To a solution of 1,3,2',6',3''-penta-N-ethoxycarbonyl-3',4'-O,O-thiocarbonyl-2''-O-benzoyl-Antibiotic JI-20B (3 gms.) in dry toluene (15 ml.) at reflux temperature under an atmosphere of argon add dropwise a solution of tri-n-butylstannane (2 gms.) and azobisisobutyronitrile (0.2 gms.) in toluene (10 ml.) over a period of one hour. Heat the reaction mixture at reflux temperature for an additional hour, then add a solution of tri-n-butylstannane (1 gm.) and azobisisobutyronitrile (0.2 gms.) in toluene (5 ml.). Continue heating the reaction mixture at reflux temperature with periodic additions of tri-n- butylstannane and azobisisobutyronitrile until thin layer chromatography of an aliquot of the reaction mixture indicates no starting material is present. Evaporate the reaction mixture to a volume of about 25 ml., then add the concentrated solution to stirred hexane (200 ml.). Separate the resultant precipitate by filtration, add dimethylsulfoxide (30 ml.) to the precipitate together with potassium hydroxide (5 gms.) in water (7.5 ml.). Stir for 24 hours, then add water (20 ml.) and heat the solution at reflux temperature for an additional 24 hours. Dilute the reaction mixture with water, adsorb the aminoglycoside onto IRC-50 (H+) resin. Pour the resin into a column, wash with water, then elute with 1 N ammonium hydroxide. Combine the like fractions containing each of the desired products as determined by thin layer chromatography, evaporate each of the combined eluates. Further purify by chromatographing each of the foregoing residues on silica gel eluting with the lower phase of a 2:1:1 chloroform: methanol:concentrated ammonia solvent system to obtain 3'-deoxy-Antibiotic JI-20B and 4'-deoxy-Antibiotic JI-20B, respectively.

C. 2'-Deoxyadenosine and 3'-Deoxyadenosine (1) 5'-O-Acetyl-2'-Deoxyadenosine and 5'-O-Acetyl-3'-Deoxyadenosine To dimethylacetamide (15 ml.) under an atmosphere of argon at reflux temperature add dropwise during a 45-minute period a solution of 5'-O-acetyl-2',3'-O,O-thiocarbonyladenosine (0.70 gms.), tri-n-butylstannane (1.17 gms.) and azobisisobutyronitrile (20 mg.) in dry dimethylacetamide (25 ml.). Continue stirring at reflux temperature adding tri-n-butylstannane (291 mg.) and azobisisobutyronitrile (10 mg.) after 2 hours and 4 hours of reaction time. Remove the solvents in vacuo, then add methanolic sodium hydroxide (25 ml., 10%) and heat this reaction at 40° C for 12 hours. Neutralize the reaction solution by careful addition of dilute hydrochloric acid (1 normal), then remove the solvents in vacuo. Dissolve the resultant solid residue (0.51 gms.) in dry pyridine (15 ml.) and add acetic anhydride (1 ml.). Allow the solution to stand at about 5° C for 12 hours, then triturate the mixture with ether, wash with water, then extract the combined ether extracts with ether, then combine the ether extracts to the original ether solution and evaporate to a residue. Chromatograph this residue on silica gel eluting with dichloromethane: methanol (increasing polarity starting from 5:1). Combine like eluates as determined by thin layer chromatography and evaporate the combined eluates to a residue to obtain 5'-O-acetyl-2'-deoxyadenosine; m.p. 150°-152° C; $[\alpha]_D^{22}$ −10° C (methanol, c=0.9) and 5'-O-acetyl-3'-deoxyadenosine; m.p. 175°-179° C; $[\alpha]_D^{22}$ −22.5° (methanol, c=0.8).

(2) 2'-Deoxyadenosine

Dissolve 5'-O-acetyl-2'-deoxyadenosine (0.200 gms.) in methanol (15 ml.), add dilute hydrochloric acid (10 ml., 1 N) and allow the reaction mixture to stand at room temperature for 24 hours. Bring the solution to a neutral pH by the careful addition of dilute sodium hydroxide (2%). Filter any precipitated salts and wash the filtrate with pyridine. Concentrate the combined filtrate and pyridine washings in vacuo and recrystallize the resultant residue from methanol:water to give 2'-deoxyadenosine; m.p. 183°-188° C; $[\alpha]_D^{22}$ −25° (water, c=0.4).

(3) 3'-Deoxyadenosine

Treat 5'-O-acetyl-3'-deoxyadenosine in a manner similar to that described in above Example 21C(2). Isolate and purify the resultant product in a manner similar to that to obtain 3'-deoxyadenosine; m.p. 183°-188° C; $[\alpha]_D^{22}$ −25° (water, c=0.4).

D. 1,2-O-Isopropylidene-3-O-Methyl-5-Deoxy-α-D-Glucofuranose

To a solution of 1,2-O-isopropylidene-3-O-methyl-5,6-O-thiocarbonyl-α-D-glucofuranose (0.3 gms.) in dry toluene (20 ml.) at reflux temperature under an atmosphere of argon add dropwise a solution of tri-n-butylstannane (0.6 gms.) and azobisisobutyronitrile (0.1 gms.) in toluene (15 ml.) over a period of one hour. Heat the reaction mixture at reflux temperature for an additional hour, then add periodically additional tri-n-butylstannane and azobisisobutyronitrile in toluene while keeping the reaction mixture at reflux temperature. Evaporate the reaction mixture, dissolve the resultant residue in dimethylsulfoxide and add potassium hydroxide in water. Stir for 24 hours, then remove the solvent in vacuo. Chromatograph the resultant residue on silica gel eluting with petroleum ether. Combine the like eluates and evaporate to a residue comprising 1,2-O-isopropylidene-3-O-methyl-5-deoxy-α-D-glucofuranose; $[\alpha]_D^{22}$ −49° (C, 2.1 in CHCl$_3$).

We claim:

1. The process for removing a secondary hydroxyl group from an organic compound having at least one secondary hydroxyl group and having any amino groups protected, which comprises the reaction of an O-alkylthio ester or an O-alkylseleno ester of said secondary alcohol with at least a molar equivalent of an organotin hydride in an inert, aprotic solvent at a temperature of at least about 100° C and under an inert atmosphere; said O-alkylthio ester being a compound of formula A or B, and said O-alkylseleno ester being a compound of formula C:

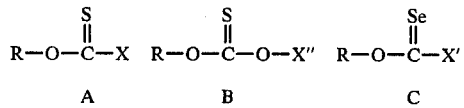

wherein R is the radical of an organic compound bonded to the oxygen by a methine carbon; X is hydrogen or an aliphatic, alicyclic or aromatic radical which may contain hetero atoms and which is bonded to the thiocarbonyl group through a carbon, nitrogen or sulfur atom; X" is either an aliphatic, alicyclic or aromatic radical which may contain hetero atoms, or is a chemical bond to a carbon atom of the radical R, said carbon atom being in a position α or β relative to the said methine carbon; and X' is an aromatic radical;

with the proviso that when said O-alkylthio ester is a compound of formula B, said reaction is carried out in the presence of a radical initiator which decomposes at about 100° C;

whereby said O-alkylthio ester group or said O-alkylseleno ester group is replaced by hydrogen to form a deoxy derivative of said organic compound.

2. The process of claim 1 wherein said organotin hydride is tri-n-butylstannane.

3. The process of claim 1 wherein any amino groups present in said organic compound are protected by a member selected from the group consisting of benzyloxycarbonyl, alkoxybenzyloxycarbonyl, alkoxycarbonyl, and alkanoyl; said organotin hydride is tri-n-butylstannane; said O-alkylthio ester is a cyclic diol thiocarbonate ester of formula B with X" being a chemical bond to a carbon atom of the radical R; and said radical initiator is a member selected from the group consisting of dibenzoyl peroxide and azobisisobutyronitrile; including the added subsequent step of subjecting the thereby formed deoxy derivative to alkaline hydrolysis.

4. The process of claim 1 wherein any amino groups present in said organic compound are protected by a member selected from the group consisting of benzyloxycarbonyl, alkoxybenzyloxycarbonyl, alkoxycarbonyl, and alkanoyl; said organotin hydride is tri-n-butylstannane; and said O-alkylthio ester is a compound of formula A selected from the group consisting of an O-sec.-alkylthiobenzoate, an O-sec.-alkyl-S-methylxanthate, and N-(sec.-alkoxythiocarbonyl)imidazole ester.

5. The process of claim 1 wherein said organic compound having at least one secondary hydroxyl group and having protected amino groups, also has any primary hydroxyl and other secondary hydroxyl groups protected.

6. The process of claim 1 wherein said organic compound having at least one secondary hydroxyl group is a 4-O-aminoglycosyl-6-O-garosaminyl-2-deoxystreptamine having amino functions protected by a member selected from the group consisting of benzyloxycarbonyl, alkoxy benzyloxycarbonyl, alkoxycarbonyl and alkanoyl;
wherein said O-alkylthio ester is an O-sec.-alkyl thiobenzoate of formula A; and
wherein said organotin hydride is tri-n-butylstannane.

7. The process of claim 5 including the added subsequent steps of removing said amino and hydroxyl protecting groups, wherein said organotin hydride is tri-n-butylstannane and wherein said O-alkylthio ester of formula A is 1,3,2',6',3''-penta-N-ethoxycarbonyl-3'-O-thiobenzoyl-2''-O-benzoyl-Antibiotic JI-20B or 1,3,2',6',3''-penta-N-ethoxycarbonyl-3'-O-thiobenzoyl-2''-O-benzoyl-Antibiotic JI-20A, whereby is obtained 3'-deoxy-Antibiotic JI-20B or 3'-deoxy-Antibiotic JI-20A, respectively.

8. The process of claim 5 including the added subsequent steps of removing said amino and hydroxy protecting groups, wherein said organotin hydride is tri-n-butylstannane and wherein said O-alkylthio ester of formula A is 1,3,2',6',3''-penta-N-ethoxycarbonyl-4'-O-thiobenzoyl-2''-O-benzoyl-Antibiotic JI-20B or 1,3,2',6',3''-penta-N-ethoxycarbonyl-4'-O-thiobenzoyl-2''-O-benzoyl-Antibiotic JI-20A, whereby is obtained 4'-deoxy-Antibiotic JI-20B or 4'-deoxy-Antibiotic JI-20A, respectively.

9. The process of claim 6 including the added subsequent step of removing said amino protecting groups, wherein said O-alkylthio ester of formula A is 1,3,6',3''-tetra-N-benzyloxycarbonyl-3'-O-thiobenzoylgentamicin B, whereby is obtained 3'-deoxygentamicin B.

10. The process of claim 5 including the added subsequent steps of removing said amino and hydroxyl protecting groups, wherein said organic hydride is tri-n-butylstannane and wherein said O-alkylthio ester of formula A is 1,3,2'-tri-N-benzyloxycarbonyl-5,6-O-cyclohexylidene-3'-O-thiobenzoyl-4',6'-O,N-carbonylneamine or 1,3,2'-tri-N-ethoxycarbonyl-5,6;4',6'-di-O-isopropylidene-3'-O-thiobenzoylparomamine, whereby is obtained 3'-deoxyneamine or 3'-deoxyparomamine, respectively.

* * * * *

UNITED STATES PATENT OFFICE
CERTIFICATE OF CORRECTION

Patent No. 4,078,139          Dated March 7, 1978

Inventor(s) Derek H. R. Barton et al

It is certified that error appears in the above-identified patent and that said Letters Patent are hereby corrected as shown below:

Column 4, line 59, "-5,6,4'-di-Q-" should read ---5,6;4',6'-di-O---
Column 7, line 29, "-dimethyl-β-chloro-" should read ---dimethyl-α-chloro---; line 52, "charged imidium" should read ---charged imidinium---; line 54, "-dimethyl-β-chloro-" should read ---dimethyl-α-chloro---. Column 8, line 9, "-dimethyl-β-chloro-" should read ---dimethyl-α-chloro---; line 10, "-dimethyl-β-chloro-" should read ---dimethyl-α-chloro---. Column 10, line 66, "-benzamide 81.5 gm.)" should read ---benzamide (1.5 gm.)---. Column 12, line 64, "B. Q-Lanosteryl-" should read ---B. O-Lanosteryl---. Column 13, line 26, "either solution" should read ---ether solution; line 40, "A. Q-Cholesteryl-" should read ---A. O-Cholesteryl---. Column 14, line 14, "solution or pyridine" should read ---solution of pyridine---. Column 28, line 18, "-3-Deoxy-2-Q-" should read ---3-Deoxy-2-O---. Column 31, line 8, "$C_{19}N_{37}N_5O_6$" should read ---$C_{19}H_{37}N_5O_6$---. Column 32, line 42, "=4Hz, 1, $H_1$")" should read ---=4Hz, 1, $H_1$')---; line 66, "($H^{30}$)" should read ---($H^{\oplus}$)---. Column 33, line 8, "($OH^{31}$)" should read ---($OH^{\ominus}$)---. Column 35, line 36, "KI-20A" should read ---JI-20A---; line 37, "aqeuous" should read ---aqueous---; line 63, "A. 1,3,2'-Tir-" should read ---A. 1,3,2'-Tri---.

*Signed and Sealed this*

*Sixteenth* Day of *January 1979*

[SEAL]

Attest:

RUTH C. MASON
*Attesting Officer*

DONALD W. BANNER
*Commissioner of Patents and Trademarks*